United States Patent [19]

Ito et al.

[11] Patent Number: 5,334,594
[45] Date of Patent: Aug. 2, 1994

[54] AMPHOTERIC TRICYCLIC COMPOUND

[75] Inventors: Yasuo Ito, Katsuyama; Hideo Kato, Fukui; Shingo Yasuda, Katsuyama; Noriyuki Kado, Katsuyama; Nobuhiko Iwasaki, Katsuyama; Hiroyuki Nishino, Katsuyama; Makoto Takeshita, Katsuyama, all of Japan

[73] Assignee: Hokoriku Pharmaceutical Co., Ltd., Katsuyama, Japan

[21] Appl. No.: 15,812

[22] Filed: Feb. 10, 1993

[30] Foreign Application Priority Data

Feb. 20, 1992 [JP] Japan .................................. 4-069404
May 1, 1992 [JP] Japan .................................. 4-137602
May 1, 1992 [JP] Japan .................................. 4-137605
Sep. 18, 1992 [JP] Japan .................................. 4-273506
Nov. 6, 1992 [JP] Japan .................................. 4-321467

[51] Int. Cl.$^5$ ................ C07D 491/052; A61K 31/445
[52] U.S. Cl. ........................................ 514/291; 546/89
[58] Field of Search ........................... 546/89; 514/291

[56] References Cited

FOREIGN PATENT DOCUMENTS

WO03138 5/1988 PCT Int'l Appl. .
WO10369 11/1989 PCT Int'l Appl. .

OTHER PUBLICATIONS

The Merck Index, 11th edition, Azatadine, 917, p. 144, (1989).

The Merck Index, 11th edition, Loratadine, 5455, p. 877 (1989).

*Primary Examiner*—Marianne M. Cintins
*Assistant Examiner*—Phyllis G. Spivack
*Attorney, Agent, or Firm*—Cushman, Darby & Cushman

[57] ABSTRACT

Novel amphoteric tricyclic compound represented by the following formula:

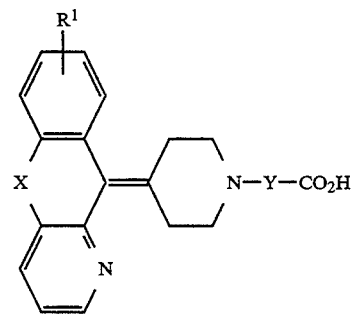

wherein $R^1$ represents a hydrogen atom or a halogen atom; X represents —O—, —CH$_2$O—, or —OCH$_2$—; and Y represents a C$_2$–C$_5$ alkylene group which may optionally be substituted with a lower alkyl group, and a pharmacologically acceptable salt thereof are disclosed. Also disclosed are a pharmaceutical composition comprising the same and a method for treatment of an allergic disease or bronchial asthma.

9 Claims, No Drawings

AMPHOTERIC TRICYCLIC COMPOUND

BACKGROUND OF THE INVENTION

1. Field of the Invention

The present invention relates to novel amphoteric tricyclic compounds and pharmacologically acceptable salts thereof which have antihistaminic activity and antiallergic activity and are useful as medicaments for the treatment of bronchial asthma, allergic rhinitis, dermatosis, urticaria and the like.

The present invention also relates to a method for preparing the amphoteric tricyclic compound, a pharmaceutical composition useful for the treatment of allergic diseases and bronchial asthma which comprises an effective amount of the amphoteric tricyclic compound, and a method for treatment allergic diseases and bronchial asthma comprising the step of administering an effective amount of the amphoteric tricyclic compound to a patient.

2. Description of the Related Art

Several antihistaminic agents and antiallergic agents are known which are characterized to have tricyclic structures. Examples of tricyclic compounds having a pyridine nucleus include clinically available Azatadine (The Merck Index, 11th edition, 917) represented by the following formula:

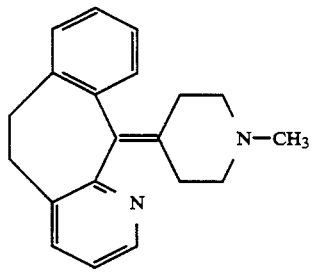

and Loratadine (The Merck Index, 11th edition, 5455) represented by the following formula.

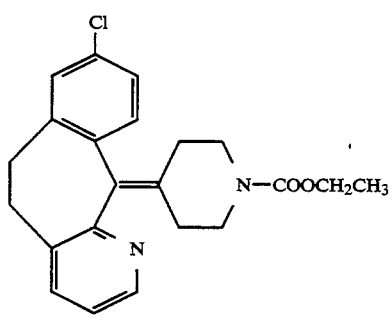

Furthermore, as compounds useful for the treatment of allergic diseases, WO89/10369 discloses, for example, the compounds represented by the following formula:

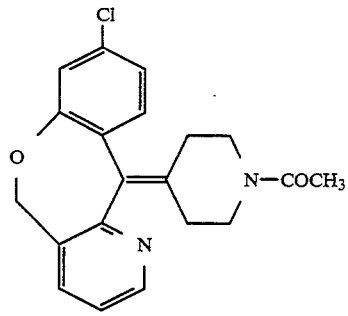

and WO88/3138 discloses, for example, the compounds represented by the following formula.

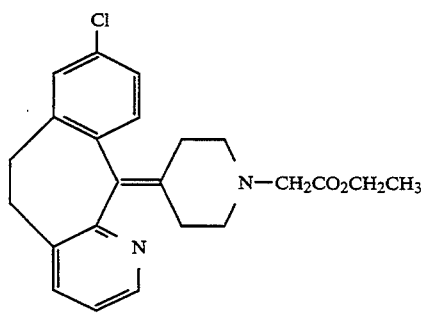

All of these compounds are characterized as being basic type compounds. Tricyclic compounds which are amphoteric and have both a basic amino group and an acidic carboxyl group in their molecule have never been prepared so far and their features of pharmacological activities have not been reported.

Numbers of antihistaminic agents have been clinically developed and are used for the treatment of allergic dermatosis and rhinitis. However, they cannot be fully satisfactory from a safe point of view and problems are remained unsolved since they could cause adverse reactions such as sleepiness, sedation, hydrodipsia, mydriasis, palpitation, and arrhythmia because of their undesirable pharmacological activity of the inhibition of central nervous system, antiacetylcholinergic activity, activity against cardiovascular system or the like. Under these circumstances, clinical development of new antihistaminic agents and antiallergic agents have been desired which extensively eliminate these problems.

SUMMARY OF THE INVENTION

An object of the present invention is to provide novel amphoteric tricyclic compounds having an improved antihistaminic and antiallergic activity.

Another object of the present invention is to provide novel amphoteric tricyclic compounds which extensively eliminate undesired adverse reactions.

A further object of the present invention is to provide a method for preparing said compounds.

Yet another object is to provide a pharmaceutical composition comprising an effective amount of said compounds.

The inventors of the present invention considered that such adverse reactions are attributable to their basic and high-lipophilic structures, and accordingly, aimed at an amphoteric structure that is neutral as a whole and exhibits a reduced lipophilicity to achieve a lead compound. As a result, the inventors found that novel amphoteric tricyclic compounds of the present invention exhibit almost no undesirable pharmacological activity, such as the inhibition of central nervous system, antiacetylcholinergic activity and activity against cardiovascular system, which could be main cause of adverse reactions observed in the use of known antihistaminic agents.

The compounds of the present invention have excellent water solubility and exhibit prolonged pharmacological activity. The compounds of the present invention are thus highly expected to be useful as medicaments for the treatment of allergic diseases and bronchial asthma.

In accordance with the present invention, there is provided a novel amphoteric tricyclic compound represented by the following formula (I):

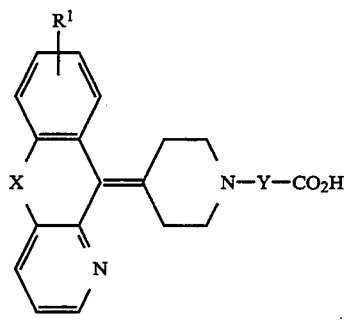

wherein $R^1$ represents a hydrogen atom or a halogen atom; X represents —O—, —$CH_2O$—, or —$OCH_2$—; and Y represents a $C_2$-$C_5$ alkylene group which may optionally be substituted with a lower alkyl group, and a pharmacologically acceptable salt thereof.

In accordance with another embodiment of the present invention, the present invention provides a method for preparing the compound represented by formula (I).

In accordance with yet another embodiment of the present invention, the present invention provides a pharmaceutical composition comprising an effective amount of the compound represented by formula (I) together with a pharmaceutically acceptable carrier or coating.

In accordance with a further embodiment, the present invention provides a method for treating an allergic disease or bronchial asthma comprising the step of administering an effective amount of the compound represented by formula (I) to an mammal.

Further objects, features and advantages of the present invention will become apparent from the Description of the Preferred Embodiment which follows, when read in light of the attached Examples and Reference Examples.

DESCRIPTION OF THE PREFERRED EMBODIMENT

In the above formula (I), a halogen atom represented by $R^1$ may be, for example, a fluorine atom, a chlorine atom, or a bromine atom. The lower alkyl group which may optionally be a substituent on the alkylene represented by Y may be, for example, methyl, ethyl, n-propyl, isopropyl, n-butyl, isobutyl, sec-butyl, or tert-butyl group. The compounds of the present invention represented by the above formula (I) may be converted to pharmacologically acceptable salts, if desired, and such salts produced may then be reconverted to produce the free compound.

The pharmacologically acceptable salts of the compounds of the present invention represented by formula (I) may be acid addition salts or alkali addition salts. Examples of the acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methansulfonate, p-toluenesulfonate, and 10-camphorsulfonate. Examples of the alkali addition salts include inorganic salts such as, for example, sodium, potassium, calcium, and ammonium salt, and organic alkali salts such as, for example, ethylenediamine, ethanolamine, N,N-dialkylethanolamine, and triethanolamine salts.

The compounds of the present invention -represented by the above-described formula (I) may include enantiomers depending on their asymmetry or diastereoisomers. These isomers and a mixture of the isomers fall within the scope of the present invention.

Preferred examples of the amphoteric tricyclic compounds of the present invention include the following compounds, however, the present invention will not be limited to these examples:

3-[4-(5,11-dihydrobenz[b]oxepino[4,3-b]pyridin-11-ylidene) piperidino]propionic acid;
4-[4-(5,11-dihydrobenz[b]oxepino[4,3-b]pyridin-11-ylidene) piperidino]butyric acid;
5-[4-(5,11-dihydrobenz[b]oxepino[4,3-b]pyridin-11-ylidene) piperidino]valetic acid;
6-[4-(5,11-dihydrobenz[b]oxepino[4,3-b ]pyridin-11-ylidene) piperidino]hexanoic acid;
3-[4-(7-fluoro-5,11-dihydrobenz[b]oxepino[4,3-b]pyridin-11-ylidene) piperidino]propionic acid;
4-[4-(7-fluoro-5,11-dihydrobenz[b]oxepino[4,3-b]pyridin-11-ylidene) piperidino]butyric acid;
5-[4-(7-fluoro-5,11-dihydrobenz[b]oxepino[4,3-b]pyridin-11-ylidene) piperidino]valetic acid;
6-[4-(7-fluoro-5,11-dihydrobenz[b]oxepino[4,3-b]pyridin-11-ylidene) piperidino]hexanoic acid
3-[4-(8-fluoro-5,11-dihydrobenz[b]oxepino[4,3-b]pyridin-11-ylidene) piperidino]propionic acid;
4-[4-(8-fluoro-5,11-dihydrobenz[b]oxepino[4,3-b]pyridin-11-ylidene) piperidino]butyric acid;
5-[4-(8-fluoro-5,11-dihydrobenz[b]oxepino[4,3-b]pyridin-11-ylidene) piperidino]valeric acid;
6-[4-(8-fluoro-5,11-dihydrobenz[b]oxepino[4,3-b]pyridin-11-ylidene) piperidino]hexanoic acid;
3-[4-(9-fluoro-5,11-dihydrobenz[b]oxepino[4,3-b]pyridin-11-ylidene) piperidino]propionic acid;
4-[4-(9-fluoro-5,11-dihydrobenz[b]oxepino[4,3-b]pyridin-11-ylidene) piperidino]butyric acid;
5-[4-(9-fluoro-5,11-dihydrobenz[b]oxepino[4,3-b]pyridin-11-ylidene) piperidino]valetic acid;
6-[4-(9-fluoro-5,11-dihydrobenz[b]oxepino[4,3-b]pyridin-11-ylidene) piperidino]hexanoic acid;
3-[4-(7-chloro-5,11-dihydrobenz[b]oxepino[4,3-b]pyridin-11-ylidene) piperidino]propionic acid;
4-[4-(7-chloro-5,11-dihydrobenz[b]oxepino[4,3-b]pyridin-11-ylidene) piperidino]butyric acid;
5-[4-(7-chloro-5,11-dihydrobenz[b]oxepino[4,3-b]pyridin-11-ylidene) piperidino]valeric acid;
6-[4-(7-chloro-5,11-dihydrobenz[b]oxepino[4,3-b]pyridin-11-ylidene) piperidino]hexanoic acid;
3-[4-(8-chloro-5,11-dihydrobenz[b]oxepino[4,3-b]pyridin-11-ylidene) piperidino]propionic acid;

4-[4-(8-chloro-5,11-dihydrobenz[b]oxepino[4,3-b]pyridin-11-ylidene) piperidino]butyric acid;
5-[4-(8-chloro-5,11-dihydrobenz[b]oxepino[4,3-b]pyridin-11-ylidene) piperidino]valeric acid;
6-[4-(8-chloro-5,11-dihydrobenz[b]oxepino[4,3-b]pyridin-11-ylidene) piperidino]hexanoic acid;
3-[4-(9-chloro-5,11-dihydrobenz[b]oxepino[4,3-b]pyridin-11-ylidene) piperidino]propionic acid;
4-[4-(9-chloro-5,11-dihydrobenz[b]oxepino[4,3-b]pyridin-11-ylidene) piperidino]butyric acid;
5-[4-(9-chloro-5,11-dihydrobenz[b]oxepino[4,3-b]pyridin-11-ylidene) piperidino]valetic acid;
6-[4-(9-chloro-5,11-dihydrobenz[b]oxepino[4,3-b]pyridin-11-ylidene) piperidino]hexanoic acid;
3-[4-(8-bromo-5,11-dihydrobenz[b]oxepino[4,3-b]pyridin-11-ylidene) piperidino]propionic acid;
4-[4-(8-bromo-5,11-dihydrobenz[b]oxepino[4,3-b]pyridin-11-ylidene) piperidino]butyric acid;
5-[4-(8-bromo-5,11-dihydrobenz[b]oxepino[4,3-b]pyridin-11-ylidene) piperidino]valeric acid;
6-[4-(8-bromo-5,11-dihydrobenz[b]oxepino[4,3-b]pyridin-11-ylidene) piperidino]hexanoic acid;
3-[4-(10H-benzo[b]pyrano[3,2-b]pyridin-10-ylidene)-piperidino]propionic acid;
4-[4-(10H-benzo[b]pyrano[3,2-b]pyridin-10-ylidene)-piperidino]butyric acid;
5-[4-(10H-benzo[b]pyrano[3,2-b]pyridin-10-ylidene)-piperidino]valeric acid;
6-[4-(10H-benzo[b]pyrano[3,2-b]pyridin-10-ylidene)-piperidino]hexanoic acid;
3-[4-(10H-7-fluorobenzo[b]pyrano[3,2-b]pyridin-10-ylidene) piperidino]propionic acid;
4-[4-(10H-7-fluorobenzo[b]pyrano[3,2-b]pyridin-10-ylidene) piperidino]butyric acid;
5-[4-(10H-7-fluorobenzo[b]pyrano[3,2-b]pyridin-10-ylidene) piperidino]valeric acid;
6-[4-(10H-7-fluorobenzo[b]pyrano[3,2-b]pyridin-10-ylidene) piperidino]hexanoic acid;
3-[4-(10H-8-fluorobenzo[b]pyrano[3,2-b]pyridin-10-ylidene) piperidino]propionic acid;
4-[4-(10H-8-fluorobenzo[b]pyrano[3,2-b]pyridin-10-ylidene) piperidino]butyric acid;
5-[4-(10H-8-fluorobenzo[b]pyrano[3,2-b]pyridin-10-ylidene) piperidino]valetic acid;
6-[4-(10H-8-fluorobenzo[b]pyrano[3,2-b]pyridin-10-ylidene) piperidino]hexanoic acid;
3-[4-(10H-7-chlorobenzo[b]pyrano[3,2-b]pyridin-10-ylidene) piperidino]propionic acid;
4-[4-(10H-7-chlorobenzo[b]pyrano[3,2-b]pyridin-10-ylidene) piperidino]butyric acid;
5-[4-(10H-7-chlorobenzo[b]pyrano[3,2-b]pyridin-10-ylidene) piperidino]valeric acid;
6-[4-(10H-7-chlorobenzo[b]pyrano[3,2-b]pyridin-10-ylidene) piperidino]hexanoic acid;
3-[4-(10H-8-chlorobenzo[b]pyrano[3,2-b]pyridin-10-ylidene) piperidino]propionic acid;
4-[4-(10H-8-chlorobenzo[b]pyrano[3,2-b]pyridin-10-ylidene) piperidino]butyric acid;
5-[4-(10H-8-chlorobenzo[b]pyrano[3,2-b]pyridin-10-ylidene) piperidino]valeric acid;
6-[4-(10H-8-chlorobenzo[b]pyrano[3,2-b]pyridin-10-ylidene) piperidino]hexanoic acid;
3-[4-(5,11-dihydrobenz[b]oxepino[4,3-b]pyridin-11-ylidene)piperidino]-2-methylpropionic acid;
4-[4-(5,11-dihydrobenz[b]oxepino[4,3-b]pyridin-11-ylidene)piperidino]-3-methylbutyric acid;
3-[4-(8-fluoro-5,11-dihydrobenz[b]oxepino[4,3-b]pyridin-11-ylidene) piperidino]-2-methylpropionic acid;
4-[4-(8-fluoro-5,11-dihydrobenz[b]oxepino[4,3-b]pyridin-11-ylidene) piperidino]-3-methylbutyric acid;
3-[4-(8-chloro-5,11-dihydrobenz[b]oxepino[4,3-b]pyridin-11-ylidene) piperidino]-2-methylpropionic acid;
4-[4-(8-chloro-5,11-dihydrobenz[b]oxepino[4,3-b]pyridin-11-ylidene) piperidino]-3-methylbutyric acid;
3-[4-(10H-benzo[b]pyrano[3,2-b]pyridin-10-ylidene)-piperidino]-2-methylpropionic acid;
4-[4-(10H-benzo[b]pyrano[3,2-b]pyridin-10-ylidene)-piperidino]-3-methylbutyric acid;
3-[4-(10H-7-fluorobenzo[b]pyrano[3,2-b]pyridin-10-ylidene)piperidino]-2-methylpropionic acid;
4-[4-(10H-7-fluorobenzo[b]pyrano[3,2-b]pyridin-10-ylidene)piperidino]-3-methylbutyric acid;
3-[4-(10H-7-chlorobenzo[b]pyrano[3,2-b]pyridin-10-ylidene)piperidino]-2-methylpropionic acid; and
4-[4-(10H-7-chlorobenzo[b]pyrano[3,2-b]pyridin-10-ylidene)piperidino ]-3-methylbutyric acid.

The novel amphoteric tricyclic compounds of the present invention represented by formula (I) can be prepared by a method set out below according to an embodiment of the present invention.

More specifically, the compounds of the present invention can be prepared by the process comprising the steps of reacting a compound represented by the following formula (II):

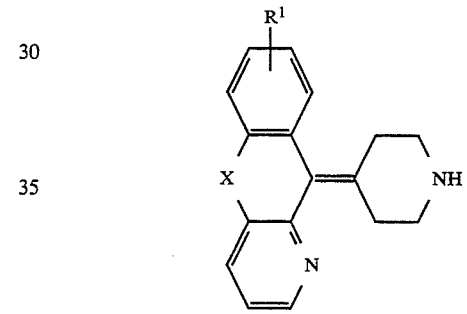

wherein $R^1$ and X are the same as those defined above, with a compound represented by the following formula (III):

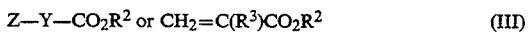

Z—Y—CO$_2$R$^2$ or CH$_2$=C(R$^3$)CO$_2$R$^2$     (III)

wherein Y is the same as that defined above; $R^2$ represents a lower alkyl group, $R^3$ represents a hydrogen atom or a lower alkyl group; and Z represents a halogen atom, in a solvent or without a solvent in the presence or absence of a base as a dehydrohalogenating agent to carry out N-alkylation, and then hydrolyzing the resulting compound.

Examples of organic solvents used for N-alkylation of the above-described method include, for example, alcohols such as methanol, ethanol, n-propanol, isopropanol, and n-butanol; aromatic hydrocarbons such as benzene, toluene, and xylene; and aprotic polar solvents such as tetrahydrofuran, 1,4-dioxane, acetonitrile, N,N-dimethylformamide, N-methyl-2-pyrrolidone, and dimethyl sulfoxide. Examples of the base used include, for example, metallic sodium, sodium hydride, sodium alkoxide, sodium amide, sodium hydroxide, potassium hydroxide, sodium carbonate, potassium carbonate, sodium hydrogen carbonate, and potassium hydrogen carbonate. The reaction may be carried out at from an ice-cooling temperature to a refluxing temperature of a solvent.

The hydrolysis reaction is carried out by using an acid or a base. For an acidic hydrolysis, such acid as hydrochloric acid, hydrobromic acid, and sulfuric acid may be used. For alkaline hydrolysis, such base as sodium hydroxide, potassium hydroxide, sodium carbonate, or potassium carbonate may be used. These acids and bases may be used as aqueous solutions, or alternatively, as solutions in a solvent such as methanol, ethanol, n-propanol, isopropanol, n-butanol, sec-butanol, tert-butanol, or acetic acid which may optionally be added with water. The reaction may be carried out at from an ice-cooling temperature to a refluxing temperature of a solvent.

The compound represented by the above-described formula (II) that is used as a starting material in the process of the present invention can be prepared according to the scheme set out below, wherein $R^1$ and X are the same as those defined above; $R^4$ represents a lower alkyl group which may optionally be substituted with a halogen atom; and Z' and Z'' independently represents a halogen atom. The preparation procedure will be explained in detail in the appended reference examples. Some of these compounds are publically known as disclosed in WO89/10369.

Scheme

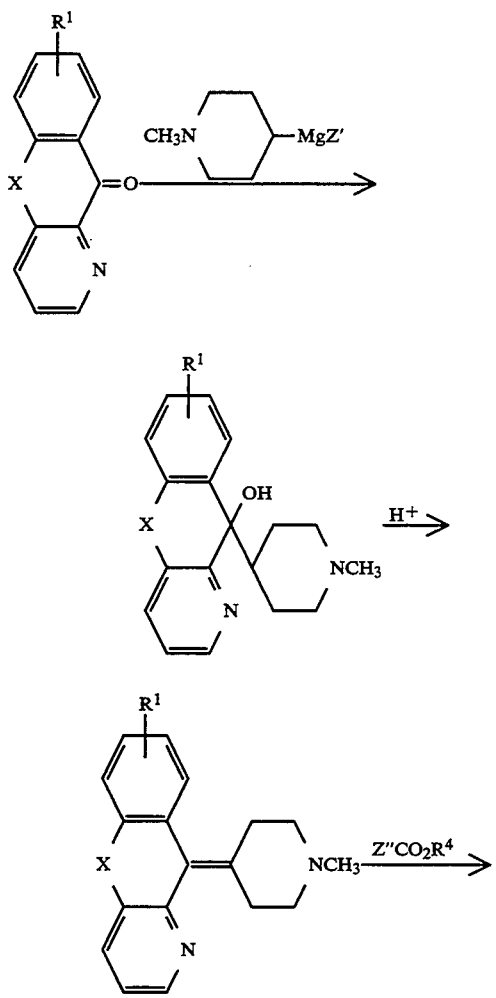

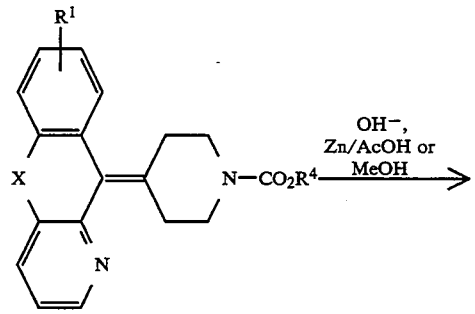

The novel amphoteric tricyclic compounds of the present invention and their pharmacologically acceptable salts may be administered orally or parenterally to a patient preferably as a pharmaceutical composition which comprises an effective amount of said compound or the salt thereof together with a pharmacologically acceptable carrier or coating. The pharmaceutical composition can be administered as composition for oral administrations such as, for example, tablet, capsule, powder, subtilized granule, granule, or syrup, or alternatively, as compositions for parenteral administration such as, for example, injection, suppository, eye drop, eye ointment, ear drop, or a composition for topical application. These pharmaceutical compositions can be prepared by an ordinary method by using pharmacologically and pharmaceutically acceptable carriers or coatings. More specifically, for the pharmaceutical composition for oral administration and suppository, an excipient such as, for example, lactose, D-mannitol, starch, or crystalline cellulose; a disintegrant such as, for example, carboxymethylcellulose or calcium carboxymethylcellulose; a binder such as, for example, hydroxypropylcellulose, hydroxyp ropylmethylcellulose, or polyvinylpyrrolidone; a lubricant such as, for example, magnesium stearate or talc; a coating agent such as, for example, hydroxypropylmethylcellulose, sucrose, or titanium oxide; a base such as, for example, polyethyleneglycol or hard fat may be used. For the injection, eye drop, or ear drop, a solubilizing agent or a solubilizer such as, for example, distilled water for injection, saline, or propylene glycol which is useful for an aqueous composition or a composition for preparing aqueous solution before use; a pH adjusting agent such as, for example, an inorganic or organic acid or an inorganic or organic base; an isotonicity agent such as, for example, sodium chloride, glucose, or glycerin; and a stabilizer may be used. For eye ointment and a composition for topical application, ingredients suitable for ointments, creams, and cataplasmas such as white vaseline, macrogol, glycerol, cloth, gelatin, polyvinylalcohol, methylcellulose, kaolin, sodium phlyacrylate, polybutene, and purified water may be used.

The dose of the pharmaceutical composition for an adult patient may generally be from about 1 to 500 mg per day for oral administration, which may be increased or decreased depending on the conditions of the patient to be treated.

Phamacological Action

The following examples demonstrate the excellent pharmacological activities of the compounds of the present invention. The results of (1) inhibitory effect on compound 48/80-induced lethality in rats with the monitoring of antihistaminic ($H_1$) activity, (2) inhibitory effects on 48 h homologous passive cutaneous anaphylaxis (PCA) in rats with the monitoring of antiallergic activity, (3) inhibitory effects on histamine-induced bronchoconstriction in anesthetized guinea-pigs with the monitoring of antiasthmatic activity, (4) inhibitory effects on ex vivo [$^3$H]-mepyramine binding to guinea-pig cerebral cortex with the monitoring of degree of penetration into brain, and (5) inhibition of [$^3$H]-QNB binding to rat cerebral cortex membrane with the monitoring of one of the undesirable side effects are summarized in Tables 1 to 3. The compounds set out below were used as the reference compounds.

Reference compound A: Azatadine
Reference compound B: Loratadine
Reference compound C: Compound represented by the following formula disclosed in WO89/10369:

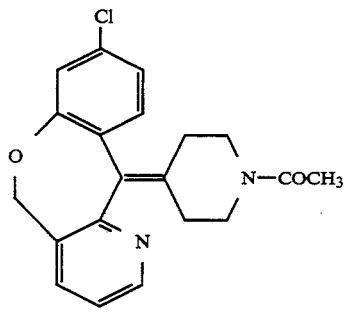

Reference compound D: Compound represented by the following formula disclosed in WO88/3138:

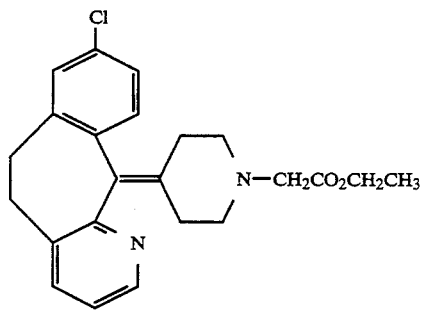

1. Inhibitory Effects on Compound 48/80-Induced Lethality in Rats (Antihistaminic Activity)

The evaluation of antihistaminic activity was carried out according to the method of Niemegeers et al. (Arch. Int. Pharmacodyn. Ther., 234, 164 (1978)).

Male Wistar rats, 6 weeks of age, were used in the experiments. Compound 48/80 (formaldehyde condensation product of p-methoxy-N-methylphenethylamine) was administered intravenously to rats at a lethal dose of 1 mg/kg. Survival rates were determined according to an all or non criteria by using the numbers of rats that survived after two hours. Test compounds (1 mg/kg) were administered orally to rats one hour before the administration of compound 48/80. Results are shown in Table 1.

TABLE 1

| | Antihistaminic activity | | |
|---|---|---|---|
| Test compound | Survival rate (%) | Test compound | Survival rate (%) |
| Example 1-(2) | 80 | Example 14-(2) | 100 |
| Example 2-(2) | 100 | Example 18-(2) | 80 |
| Example 4-(2) | 100 | Example 20-(2) | 100 |
| Example 5-(2) | 100 | Example 21-(2) | 100 |
| Example 6-(2) | 100 | Example 23-(2) | 100 |
| Example 8-(2) | 100 | Reference compound A | 60 |
| Example 9-(2) | 100 | Reference compound B | 60 |
| Example 10-(2) | 100 | Reference compound C | 20 |
| Example 11-(2) | 100 | Reference compound D | 40 |
| Example 12-(2) | 100 | | |

It can be understood that the compounds of the present invention are more potent in antihistaminic activity than the reference compounds.

2. Inhibitory Effects on 48 h Homologous Passive Cutaneous Anaphylaxis (PCA) in Rats (Antiallergic Activity)

The induction and evaluation of antiallergic activity were carried out according to the method of Makino et al. (Japan J. Pharmacology, 52, 87 (1990)).

Male Wistar rats, 6 weeks of age, were passively sensitized by intracutaneous injection on the back at a volume of 0.1 ml of 20- or 40-fold diluted anti-DNP-As rat serum. After 48 hours, the animals were challenged by an intravenous injection of 0.5 ml saline solution containing 1 mg of DNP-As and 5 mg of Evans blue. The animals were sacrificed 30 minutes after the challenge and then the extravasated dye was extracted with 1N KOH and acetone. After neutralization with 1N $H_3PO_4$, the amount of dye was determined by measuring the absorbance of the extract at 620 nm. Test compounds (1 mg/kg) were orally administered to rats one hour before the antigen challenge. The inhibitory activity of test compounds were obtained as percent inhibition of PCA by comparing the results obtained from control rats. Results are shown in Table 2.

3. Inhibitory Effects on Histamine-Induced Bronchoconstriction in Anesthetized Guinea-Pigs (Antiasthmatic Activity)

The induction and evaluation of antiasthmatic activity were carried out according to the method of Makino et al. (J. Pharm. Pharmacol., 42, 236 (1990)).

Male Hartley guinea-pigs, 6 weeks of age, were anesthetized with urethane ( 1.5 g/kg, i.p. ). The carotid artery and jugular vein were cannulated to measure arterial blood pressure and to facilitate intravenous histamine administration. The trachea was cannulated and the animals were ventilated using a respiratory pump (60 strokes/min; 4 ml/stroke). Changes in insufflation pressure induced by the administration of histamine (20 μg/kg, i.v.) at a constant airflow were constantly monitored as percentage values based on the maximum pressure (100%) (Bronchospasm tramsducer 7020, Ugo Basile). Test compounds were administered orally to animals two hours before the administration of histamine. The $ED_{50}$ values (doses which induce 50% inhibition of histamine-induced broncho-constriction compared to inhibition observed in control) were calculated using dose-inhibition curves. Results are shown in Table 2.

4. Inhibitory Effects on Ex Vivo [$^3$H]-Mepyramine Binding to Guinea-Pig Cerebral Cortex (Degree of Penetration into Brain)

The evaluation of histamine (H$_1$) receptor affinity on guinea-pig cerebral cortex was carried out according to the method of Ahn et al. (Eur. J. Pharmacol., 127, 153 (1986)).

Male Hartley guinea-pigs, 6 weeks of age, were administered orally with test compounds or vehicles. After two hours, animals were killed by exsanguination and brains were rapidly isolated. Separated cerebral cortices were homogenized in 50-folds volume of 50 mM Na/K-phosphate buffer (pH 7.4). These homogenates were used as crude membrane fractions for receptor binding assay. [$^3$H]-mepyramine was used as a radioactive ligand. Non-specific binding was observed in the presence of promethazine (1 μM). The ID$_{50}$ values (doses which induce 50% inhibition of specific binding of vehicle treated group) were calculated using dose-inhibition curves. Results are shown in Table 2.

TABLE 2

Antiallergic activity, antiasthmatic activity and degree of penetration into brain

| Test compound | Antiallergic activity (A) inhibition (%) | Antiasthmatic activity (B) ED$_{50}$ (mg/kg) |
|---|---|---|
| Example 1-(2) | 80 | 0.082 |
| Example 2-(2) | 78 | 0 046 |
| Example 5-(2) | 79 | 0.023 |
| Reference compound A | 77 | 0.001 |
| Reference compound B | 38 | 0.13 |
| Reference compound C | −11 | No effect (1 mg/kg) |
| Reference compound D | 41 | 0.29 |

| Test compound | Degree of penetration activity (A) ID$_{50}$ (mg/kg) | Selectivity (C/B) |
|---|---|---|
| Example 1-(2) | 36 | 439 |
| Example 2-(2) | 32 | 696 |
| Example 5-(2) | 53 | 2304 |
| Reference compound A | 0.028 | 28 |
| Reference compound B | 10 | 77 |
| Reference compound D | 11 | 38 |

It can be concluded that the compounds of the present invention have excellent antiallergic and antiasthmatic activities and are almost totally unable to penetrate into brain. The values of the selectivity (C/B) also indicate that the compounds of the present invention are safe compounds.

5. Inhibition of [$^3$H]-QNB Binding to Rat Cerebral Cortex Membrane (Muscarinic Acetylcholine Receptor Binding Assay)

The evaluation of muscarinic acetylcholine receptor affinity on rat cerebral cortex membrane was carried out according to the method of Yamamura et al. (Proc. Natl. Acad. Sci., USA, 71, 1725, 1974).

[$^3$H]-QNB (Quinuclidinyl benzilate) was used as radioactive ligand. Non-specific binding was observed in the presence of attopine (1 μM). The IC$_{50}$ values (concentration which produces 50% inhibition of specific binding) were calculated using concentration-inhibition curves. Dissociation constants (Ki) of the test compounds were calculated by the equation of Cheng and Prusoff. The pKi values are indicated as negative log value of Ki (−log Ki). Results are shown in Table 3.

TABLE 3

Muscarinic acetylcholine receptor binding assay.

| Test compound | pKi |
|---|---|
| Example 2-(2) | <5 |
| Example 5-(2) | <5 |
| Reference compound A | 8.47 |
| Reference compound B | 6.04 |
| Reference compound C | 5.72 |
| Reference compound D | 5.84 |

It can be concluded that the compounds of the present invention have almost no affinity to muscarinic acetylcholine receptor which would cause undesirable side effects such as suppression of secretion from bronchial gland, thirst, mydriasis, anuresis and coprostasis.

From the foregoing results, one of ordinary skill in the art can readily understand that the compounds of the present invention have excellent antihistaminic, antiallergic, and antiasthmatic activities, and are almost totally unable to penetrate into brain. It can also be understood that the compounds of the present invention have reduced side effects caused by the inhibition of central nervous system and the affinity to muscarinic acetylcholine receptor, and the compounds of the present invention are thus useful for the treatment of various allergic disorders, for instance, bronchial asthma, rhinitis, conjunctivitis, dermatitis, and urticaria.

EXAMPLES

The present invention will be further illustrated by the following References and Examples. The examples are given by way of illustration only and all not be construed as limiting.

Reference Example 1: 2-Cyano-3-(3-fluorophenoxymethyl)pyridine

To a chilled solution of sodium ethoxide, prepared from 13.8 g of sodium metal and 240 ml of absolute ethanol, 56.9 ml of 3-fluorophenol was added and the mixture was stirred at room temperature for 30 minutes. Crude 3-bromomethyl-2-cyanopyridine (103 g) was added to the mixture at 5° C., and the mixture was reflexed for 2 hours. After being concentrated, the reaction mixture was diluted with ether, and the resultant insoluble materials were removed by filtration. The filtrate was washed with 10% aqueous sodium hydroxide solution and with water, dried over anhydrous sodium sulfate, and then concentrated. The residue was crystallized by trituration with a mixture of ether and n-hexane to yield 58.0 g of pale brown crystals, which were recrystallized from isopropyl ether to give pale yellow needles, mp 52°–53° C.

Analysis for C$_{13}$H$_9$ FN$_2$O Calculated C, 68.42; H, 3.97; N, 12.27 Found C, 68.37; H, 4.03; N, 12.25.

The compounds of Reference Examples 2–5 were prepared in the same manner as described in Reference Example 1.

Reference Example 2: 2-Cyano-3-(4-fluorophenoxymethyl)pyridine

Pale yellow needles, mp 98.5°–99.5° C. (iso-Pr$_2$O)

Analysis for C$_{13}$H$_9$ FN$_2$O Calculated C, 68.42; H, 3.97; N, 12.27 Found C, 68.43; H, 4.01; N, 12.22.

Reference Example 3: 2-Cyano-3-(2-chlorophenoxymethyl)pyridine

Colorless prisms, mp 92°–93° C. ( iso-Pr$_2$O)

Analysis for $C_{13}H_9 ClN_2O$ Calculated C, 63.82; H, 3.71; N, 11.45 Found C, 63.71; H, 3.67; N, 11.41.

Reference Example 4:
2-Cyano-3-(4-chlorophenoxymethyl)pyridine

Colorless prisms, mp 76°–77° C. (iso-$Pr_2O$)

Analysis for $C_{13}H_9 ClN_2O$ Calculated C, 63.82; H, 3.71; N, 11.45 Found C, 63.88; H, 3.73; N, 11.42.

Reference Example 5:
2-Cyano-3-(3-bromophenoxymethyl)pyridine

Colorless prisms, mp 58°–59° C. (iso-PrOH)

Analysis for $C_{13}H_9 BrN_2O$ Calculated C, 54.00; H, 3.14; N, 9.69 Found C, 54.00; H, 3.07; N, 9.67.

Reference Example 6:
3-(3-Fluorophenoxy)pyridine-N-oxide

To a solution of 46.3 g of m-chloroperbenzoic acid in 460 ml of methylene chloride, 37.35 g of 3-(3-fluorophenoxy)pyridine was added at room temperature, and the mixture was stirred at room temperature for 1.5 hours. An aqueous sodium hydrogen sulfite solution (20%, 120 ml) was added to the mixture and then the mixture was stirred for a few minutes. The organic layer separated was washed with 10% aqueous sodium hydroxide solution and with water, dried over anhydrous sodium sulfate, and concentrated. The residue was crystallized by trituration with isopropyl ether. The crystals were collected by filtration and washed with isopropyl ether to yield 34.44 g of pale yellow crystals, which were recrystallized from ethyl acetate to give colorless needles, mp 59°–61° C.

Analysis for $C_{11}H_8 FNO_2$ Calculated C, 64.39; H, 3.93; N, 6.83 Found C, 64.27; H, 3.94; N, 6.68.

Reference Example 7:
2-Cyano-3-(3-fluorophenoxy)pyridine

A mixture of 33.44 g of 3-(3-fluorophenoxy)pyridine N-oxide, 64.6 ml of trimethylsilyl cyanide and 45.9 ml of triethylamine in 180 ml of acetonitrile was refluxed for 4 hours. After the reaction mixture was concentrated, 200 ml of methylene chloride and 100 ml of 2M aqueous potassium carbonate was added to the residue and the mixture was stirred for a few minutes. The organic layer separated was washed with 50 ml of water, dried over anhydrous sodium sulfate, and concentrated. The solid obtained was washed with isopropyl ether to yield 28.30 g of pale brown crystals, which were recrystallized from ethyl acetate to give slightly brown crystals, mp 92°–93° C.

Analysis for $C_{12}H_7 FN_2O$ Calculated C, 67.29; H, 3.29; N, 13.08 Found C, 67.41; H, 3.44; N, 13.12.

Reference Example 8:
8-Fluoro-5,11-dihydrobenz[b]oxepino[4,3-b]pyridin-11-one To 921 g of trifluoromethanesulfonic acid, 60.1 g of 2-cyano-3-(3-fluorophenoxymethyl)pyridine was added potionwise at 5° C., and the mixture was stirred at room temperature for 2 hours. The reaction mixture was poured into 1400 ml of ice-water. Concentrated hydrochloric acid (57.0 ml) was added to the mixture and the mixture obtained was stirred at room temperature for 16 hours. The resulting crystals were collected by filtration and then suspended in 300 ml of $H_2O$. The suspension was adjusted to pH 9 with 27.0 g of potassium carbonate and then extracted with methylene chloride. The extract was washed with brine, dried over anhydrous sodium sulfate, and concentrated to yield 42.6 g of pale red crystals, which were recrystallized from ethyl acetate to give colorless needles, mp 144°–145° C.

Analysis for $C_{13}H_8 FNO_2$ Calculated C, 68.12; H, 3.52; N, 6.11 Found C, 68.17; H, 3.68; N, 6.39.

The compounds of Reference Examples 9–13 were prepared in the same manner as described in Reference Example 8.

Reference Example 9:
9-Fluoro-5,11-dihydrobenz[b]oxepino[4,3-b]pyridin-11-one Colorless prisms, mp 145°–146° C. (AcOEt)

Analysis for $C_{13}H_8 FNO_2$ Calculated C, 68.12; H, 3.52; N, 6.11 Found C, 68.00; H, 3.61; N, 6.11.

Reference Example 10:
7-Chloro-5,11-dihydrobenz[b]oxepino[4,3-b]pyridin-11-one Colorless needles, mp 149°–150° C. (AcOEt)

Analysis for $C_{13}H_8 ClNO_2$ Calculated C, 63.56; H, 3.28; N, 5.70 Found C, 63.35; H, 3.29; N, 5.65.

Reference Example 11:
9-Chloro-5,11-dihydrobenz[b]oxepino[4,3-b]pyridin-11-one Slightly gray scales, mp 207°–208° C. (AcOEt)

Analysis for $C_{13}H_8 ClNO_2$ Calculated C, 63.56; H, 3.28; N, 5.70 Found C, 63.39; H, 3.19; N, 5.63.

Reference Example 12:
8-Bromo-5,11-dihydrobenz[b]oxepino[4,3-b]pyridin-11-one Colorless crystals, mp 144°–145° C. (AcOEt)

Analysis for $C_{13}H_8 BrNO_2$ Calculated C, 53.82; H, 2.78; N, 4.83 Found C, 53.78; H, 2.76; N, 4.83.

Reference Example 13:
7-Fluoro-10H-benzo[b]pyrano[3,2-b]pyridin-10-one

Colorless crystals, mp 220°–221° C. (AcOEt)

Analysis for $C_{12}H_6 FNO_2$ Calculated C, 66.98; H, 2.81; N, 6.51 Found C, 66.97; H, 2.82; N, 6.57.

Reference Example 14:
5,11-Dihydro-11-(1-methyl-4-piperidinyl) benz[b]oxepino[4,3-b]pyridin-11-ol To a chilled Grignard solution, prepared from 23.5 g of 4-chloro-1-methylpiperidine and 4.28 g of magnesium turnings in 60 ml of dry tetrahydrofuran, a solution of 18.5 g of 5,11-dihydrobenz[b]oxepino[4,3-b]pyridin-11-one in 100 ml of dry tetrahydrofuran was added dropwise, and the mixture was stirred at room temperature for one hour. An aqueous ammonium chloride solution (15%, 120 g) was added, and the mixture was stirred for a few minutes and then extracted with ether. The organic layer was washed with water, dried over anhydrous sodium sulfate, and concentrated. The residue obtained was purified by column chromatography on aluminium oxide (eluent: methylene chloride) to yield 10.84 g of pale yellow crystals, which were recrystallized from a mixture of benzene and isopropyl ether to give pale yellow prisms, mp 136.5°–137.5° C.

Analysis for $C_{19}H_{22}N_2 O_2$ Calculated C, 73.52; H, 7.14; N, 9.03 Found C, 73.43; H, 7.17; N, 9.08.

The compounds of Reference Examples 15–20 were prepared in the same manner as described in Reference Example 14.

Reference Example 15:
8-Fluoro-5,11-dihydro-11-(1-methyl-4-piperidinyl)-benz[b]oxepino[4,3-b]pyridin-11-ol Slightly yellow plates, mp 144°–145° C. (Benzene)
Analysis for $C_{19}H_{21}FN_2 O_2$ Calculated C, 69.49; H, 6.45; N, 8.53 Found C, 69.60; H, 6.45; N, 8.43.

Reference Example 16:
9-Fluoro-5,11-dihydro-11-(1-methyl-4-piperidinyl)-benz[b]oxepino[4,3-b]pyridin-11-ol Pale brown crystals, mp 138°–140° C. (AcOEt-iso-$Pr_2O$)
Analysis for $C_{19}H_{21}FN_2 O_2$ Calculated C, 69.49; H, 6.45; N, 8.53 Found C, 69.44; H, 6.50; N, 8.44.

Reference Example 17:
7-Chloro-5,11-dihydro-11-(1-methyl-4-piperidinyl)-benz[b]oxepino[4,3-b]pyridin-11-ol Colorless needles, mp 164°–165° C. (iso-PrOH)
Analysis $C_{19}H_{21}ClN_2 O_2$ Calculated C, 66.18; H, 6.14; N, 8.12 Found C, 66.06; H, 6.11; N, 8.05.

Reference Example 18:
9-Chloro-5,11-dihydro-11-(1-methyl-4-piperidinyl)-benz[b]oxepino[4,3-b]pyridin-11-ol Yellowish brown amorphous
IR spectrum $\nu$ (liq) $cm^{-1}$: 3312
NMR spectrum $\delta$ (CDCl$_3$) ppm: 0.74–0.84(1H,m),1.03–1.15 (1H,m),1.55–1.90(4H,m),2.22(3H,s),2.60–2.85(3H,m),4.98(1H,d,J=16 Hz), 5.48(1H,d,J=16 Hz) ,6.46(1H,s),7.03(1H,d,J=8.5 Hz),7.20(1H,dd,J=8.5, 3Hz), 7.23(1H,dd,J=7.5,5 Hz ),7.35(1H,dd,J=7.5,1 Hz ), 7.86(1H,d,J=3 Hz), 8.44(1H,dd,J=5,1 Hz)
High resolution mass spectrum for: $C_{19}H_{21}ClN_2 O_2$ Calculated m/z: 344.1292, 346.1262 Found m/z: 344.1288, 346.1260

Reference Example 19:
8-Bromo-5,11-dihydro-11-(1-methyl-4-piperidinyl)-benz[b]oxepino[4,3-b]pyridin-11-ol Pale brown crystals, mp 133°–135° C. (AcOEt)
Analysis for $C_{19}H_{21}BrN_2 O_2.\frac{1}{4}H_2O$ Calculated C, 57.95; H, 5.50; N, 7.11 Found C, 58.08; H, 5.41; N, 7.11.

Reference Example 20:
7-Fluoro-10-(1-methyl-4-piperidinyl)-10H-benzo[b]pyrano[3,2-b]pyridin-10-ol Slightly yellow amorphous
IR spectrum $\nu$ (liq) $cm^{-1}$:3072
NMR spectrum $\delta$ (CDCl$_3$) ppm: 1.12–1.19(1H,m) ,1.43–1.46 (1H,m),1.59–1.97(5H,m),2.15(3H,s),2.74–2.80(2H,m),4.31(1H,s), 6.86(1H,dd,J=9,2.5 Hz),6.94(1H,td,J=8.5,2.5 Hz),7.29(1H,dd,J=8.5, Hz),7.45(1H,dd,J=8.5,1 Hz ),7.64(1H,dd,J=8.5,6 Hz ),8.42(1H,dd,J=5, 1 Hz)
High resolution mass spectrum for: $C_{18}H_{19}FN_2 O_2$ Calculated m/z: 314.1431; Found m/z:314.1427

Reference Example 21:
5,11-Dihydro-11-(1-methylpiperidin-4-ylidene) benz[b]oxepino[4,3-b]pyridine To 9.0 g of 5,11-dihydro-11-(1-methyl-4-piperidinyl) benz[b]oxepino[4,3-b]pyridin-11-ol, trifluoromethanesulfonic acid was added dropwise at room temperature, and the mixture was stirred at room temperature for 2 hours. The reaction mixture was poured into ice-water by portions. The aqueous solution obtained was adjusted to pH 11 with 10% aqueous potassium carbonate solution and then extracted with methylene chloride. The extract was washed with water, dried over anhydrous sodium sulfate, and concentrated. The solid obtained was washed with isopropyl ether to yield 8.20 g of pale brown crystals, which were recrystallized from ethyl acetate to give pale orange needles, mp 143°–144° C.

Analysis for $C_{19}H_{20}N_2 O.\frac{1}{4} H_2O$ Calculated C, 76.87; H, 6.96; N, 9.44 Found C, 77.16; H, 6.86; N, 9.55.

The compounds of Reference Examples 22–27 were prepared in the same manner as described in Reference Example 21.

Reference Example 22:
8-Fluoro-5,11-dihydro-11-(1-methylpiperidin-4-ylidene)benz[b]oxepino[4,3-b]pyridine Pale red prisms, mp 125°–126° C. (AcOEt)
Analysis for $C_{19}H_{19}FN_2O$ Calculated C, 73.53; H, 6.17; N, 9.03 Found C, 73.30; H, 6.28; N, 9.14.

Reference Example 23:
9-Fluoro-5,11-dihydro-11-(1-methylpiperidin-4-ylidene)benz[b]oxepino[4,3-b]pyridine Colorless crystals, mp 146°–148° C. (iso-$Pr_2O$)
Analysis for $C_{19}H_{19}FN_2O$ Calculated C, 73.53; H, 6.17; N, 9.03 Found C, 73.57; H, 6.18; N, 8.89.

Reference Example 24:
7-Chloro-5,11-dihydro-11-(1-methylpiperidin-4-ylidene)benz[b]oxepino[4,3-b]pyridine Colorless prisms, mp 169°–170° C. (iso-PrOH)
Analysis for $C_{19}H_{19}ClN_2O$ Calculated C, 69.83; H, 5.86; N, 8.57 Found C, 69.87; H, 5.79; N, 8.52.

Reference Example 25:
9-Chloro-5,11-dihydro-11-(1-methylpiperidin-4-ylidene)benz[b]oxepino[4,3-b]pyridine . Dihydrochloride Colorless prisms, mp 274°–275.5° C. (decomposition) (EtOH)
Analysis for $C_{19}H_{19}ClN_2O.2HCl.2H_2O$ Calculated C, 52.37; H, 5.78; N, 6.43 Found C, 52.66; H, 5.79; N, 6.27.

Reference Example 26:
8-Bromo-5,11-dihydro-11-(1-methylpiperidin-4-ylidene)benz[b]oxepino[4,3-b]pyridine Pale brown crystals, mp 176°–178° C. (AcOEt)
Analysis for $C_{19}H_{19}BrN_2O$ Calculated C, 61.47; H, 5.16; N, 7.55 Found C, 61.38; H, 5.15; N, 7.49.

Reference Example 27:
7-Fluoro-10-(1-methylpiperidin-4-ylidene)-10H-benzo[b]pyrano[3,2-b]pyridine Pale yellowish-brown prisms, mp 99°–100° C. (iso-$Pr_2O$)
Analysis for $C_{18}H_{17}FN_2O$ Calculated C, 72.96; H, 5.78; N, 9.45 Found C, 73.05; H, 5.83; N, 9.45.

Reference Example 28: Ethyl 4-(5,11-Dihydrobenz[b]oxepino[4,3-b]pyridin-11-ylidene) piperidinocarboxylate The mixture of 7.67 g of 5,11-dihydro-11-(1-methylpiperidin-4-ylidene )benz[b]oxepino[4,3-b]pyridine and 50.2 ml of ethyl chloroformate in 150 ml of 1,2-dichloroethane was refluxed for 4 hours. After the reaction mixture was cooled, the mixture was washed with saturated sodium hydrogen carbonate solution and with water, dried over anhydrous sodium sulfate, and concentrated. The residue was purified by column chromatography on silica gel [eluent: methylene chloride - methanol (30:1)] to yield 7.86 g of brown crystals, which were recrystallized from ethyl acetate to give colorless prisms, mp 171°–173° C.

Analysis for $C_{21}H_{22}N_2O_3$ Calculated C, 71.98; H, 6.33; N, 7.99 Found C, 72.07; H, 6.31; N, 7.95.

The compounds of Reference Examples 29–33 were prepared in the same manner described in Reference Example 28.

Reference Example 29: Ethyl 4-(8-Fluoro-5,11-dihydrobenz[b]oxepino[4,3-b]pyridin-11-ylidene)piperidinocarboxylate Brown oil IR spectrum ν (liq) cm$^{-1}$: 1698

NMR spectrum δ (CDCl$_3$) ppm: 1.26(3H,t,J=7.5 Hz) ,2.28–2.64(4H,m),3.08–3.29(2H,m),3.-49–3.85(2H,m),4.15(2H,q,J=7.5 Hz), 4.85(1H,d,J=12.5 Hz),5.61(1H,d,J=12.5 Hz),6.52(1H,dd,J=10.5, 2.5 Hz ),6.59–6.62(1H,m),7.05(1H,dd ,J=8.5,7 Hz ),7.26(1H,dd ,J=7.5, 5Hz),7.69–7.71(1H,m),8.56(1H,dd,J=5,1 Hz)

High resolution mass spectrum for: $C_{21}H_{21}FN_2O_3$ Calculated m/z: 368.1536 Found m/z: 368.1526.

Reference Example 30: Ethyl 4-(9-Fluoro-5,11-dihydrobenz[b]oxepino[4,3-b]pyridin-11-ylidene )piperidinocarboxylate Pale brown amorphous IR spectrum ν (KBr) cm$^{-1}$:1698

NMR spectrum δ (CDCl$_3$) ppm: 1.11(3H,t,J=7 Hz) ,2.26–2.68(4H,m),3.08–3.31(2H,m),3.72–3.91 (2H,m), 4.13 (2H,q,J=7 Hz), 4.83 (1H, d, J=12.5 Hz), 5.56(1H, d, J=12.5 Hz),6.77(1H,dd,J=8.5,5 Hz), 6.82(1H,td,J=8.5,3 Hz),6.86(1H,ddd,J=8.5,3,1.5 Hz),7.24(1H,dd, J=8,5 Hz),7.66(1H,dd,J=8,1.5 Hz),8.56(1H,dd,J=5,1.5 Hz)

High resolution mass spectrum for: $C_{21}H_{21}FN_2O_2$ Calculated m/z: 368.1536 Found m/z: 368.1541.

Reference Example 31: Ethyl 4-(7-Chloro-5,11-dihydrobenz[b]oxepino[4,3-b]pyridin-11-ylidene)piperidinocarboxylate Pale yellow needles, mp 149.5°–151° C. (AcOEt)

Analysis for $C_{21}H_{21}ClN_2O_3$ Calculated C, 65.54; H, 5.50; N, 7.28 Found C, 65.57; H, 5.58; N, 7.19.

Reference Example 32: Ethyl 4-(9-Chloro-5,11-dihydrobenz[b]oxepino[4,3-b]pyridin-11 -ylidene)piperidinocarboxylate Colorless crystals, mp 166°–168° C. (AcOEt-iso-Pr$_2$O)

Analysis for $C_{21}H_{21}ClN_2O_3$ Calculated C, 65.54; H, 5.50; N, 7.28 Found C, 65.42; H, 5.53; N, 7.15.

Reference Example 33: Ethyl 4-(8-Bromo-5,11-dihydrobenz[b]oxepino[4,3-b]pyridin-11-ylidene)piperidinocarboxylate Slightly brown crystals, mp 163°–164° C. (AcOEt)

Analysis for $C_{21}H_{21}BrN_2O_3$ Calculated C, 58.75; H, 4.93; N, 6.53 Found C, 58.68; H, 4.87; N, 6.55.

Reference Example 34: 5,11-Dihydro-11-(4-piperidylidene) benz[b]oxepino[4,3-b]pyridine. Dihydrochloride The mixture of 6.53 g of ethyl 4-(5,11-dihydrobenz[b]oxepino[4,3-b]pyridin-11-ylidene)piperidinocarboxylate and 6.15 g of potassium hydroxide in 50 ml of isopropanol was refluxed for 19 h. After the mixture was concentrated, the residue was diluted with water and extracted with methylene chloride. The extract was washed with water, dried over anhydrous sodium sulfate, and concentrated to yield 5.66 g of a brown oil. The oil was converted to the hydrochloride in the usual manner and the salt was recrystallized from isopropanol to give pale brown crystals, mp 275°–280° C. (decomposition).

Analysis for $C_{18}H_{18}N_2O \cdot 2HCl \cdot \frac{1}{2}H_2O$ Calculated C, 60.01; H, 5.88; N, 7.78 Found C, 60.06; H, 6.15; N, 7.73.

The compounds of Reference Examples 35–39 were prepared in the same manner as described in Reference Example 34.

Reference Example 35: 8-Fluoro-5,11-dihydro-11-(4-piperidylidene) benz[b]oxepino[4,3-b]pyridine Pale yellowish-brown crystals, mp 173°–174° C. (AcOEt)

Analysis for $C_{18}H_{17}FN_2O$ Calculated C, 72.96; H, 5.78; N, 9.45 Found C, 72.71; H, 5.86; N, 9.29.

Reference Example 36: 9-Fluoro-5,11-dihydro-11-(4-piperidylidene) benz[b]oxepino[4,3-b]pyridine Pale brown crystals, mp 154°–155° C. (AcOEt)

Analysis for $C_{18}H_{17}ClN_2O$ Calculated C, 72.96; H, 5.78; N, 9.45 Found C, 72.64; H, 5.93; N, 9.33.

Reference Example 37: 7-Chloro-5,11-dihydro-11-(4-piperidylidene) benz[b]oxepino[4,3-b]pyridine Colorless crystals, mp 173°–175° C. (AcOEt)

Analysis for $C_{18}H_{17}ClN_2O$ Calculated C, 69.12; H, 5.48; N, 8.96 Found C, 68.97; H, 5.52; N, 8.79.

Reference Example 38: 9-Chloro-5,11-dihydro-11-(4-piperidylidene) benz[b]oxepino[4,3-b]pyridine Pale brown needles, mp 180°–182° C. (AcOEt)

Analysis for $C_{18}H_{17}ClN_2O$ Calculated C, 69.12; H, 5.48; N, 8.96 Found C, 69.21; H, 5.40; N, 9.00.

Reference Example 39: 8-Bromo-5,11-dihydro-11-(4-piperidylidene) benz[b]oxepino[4,3-b]pyridine Slightly brown crystals, mp. 179°–181° C. (iso-PrOH)

Analysis for $C_{18}H_{17}BrN_2O$ Calculated C, 60.52; H, 4.80; N, 7.84 Found C, 60.41; H, 4.91; N, 7.69.

Reference Example 40: 10-(4-Piperidylidene)-10H-benzo[b]pyrano[3,2-b]pyridine.Hydrochloride To a chilled mixture of 9.11 g of 10-(1-methylpiperidin-4-ylidene)-10H-benzo[b]pyrano[3,2-b]pyridine and 6.80 ml of triethylamine in 91 ml of 1,2-dichloroethane, 14.1 ml of 1-chloroethyl chloroformate was added dropwise, and the mixture was stirred at room temperature for 14 hours. The reaction mixture was washed with water and with brine, dried over anhydrous sodium sulfate, and concentrated. The residue was diluted with 91 ml of methanol and then refluxed for 1 hour. After the mixture was concentrated, the residue obtained was diluted with water. The aqueous solution was adjusted to pH 10 with 10% aqueous sodium hydroxide solution and then extracted with methylene chloride. The extract was washed with brine, dried over anhydrous sodium sulfate, and then concentrated. The residue was purified by column chromatography on aluminum oxide [eluent: methylene chloride - methanol (20:1)] to yield 8.02 g of a brown oil. The oil was converted to the hydrochloride in a usual manner and the salt was recrystallized from ethanol to give greeny brown prisms, mp 196°–199° C.

Analysis for $C_{17}H_{16}N_2O \cdot HCl$ Calculated C, 67.88; H, 5.70; N, 9.31 Found C, 67.57; H, 5.69; N, 9.19

The compound of Reference Example 41 was prepared in the same manner as described in Reference Example 40.

Reference Example 41: 7-Fluoro-10-(4-piperidylidene)-10H-benzo[b]pyrano[3,2-b]pyridine.Hydrochloride Pale brown prisms, mp 217°–219° C. (EtOH)

Analysis for $C_{17}H_{15}FN_2O \cdot HCl$ Calculated C, 64.05; H, 5.06; N, 8.79 Found C, 64.00; H, 5.10; N, 8.80.

Example 1:
3-[4-(5,11-Dihydrobenz[b]oxepino[4,3-b]pyridin-11-ylidene)piperidino]propionic Acid.Hydrochloride (1) Ethyl 3-[4-(5,11-Dihydrobenz[b]oxepino[4,3-b]pyridin-11-ylidene) piperidino]propionate The mixture of 2.45 g of 5,11-dihydro-11-(4-piperidylidene)benz[b]oxepino[4,3-b]pyridine and 1.44 ml of ethyl acrylate in 30 ml of ethanol was stirred at room temperature for 17 hours. After the reaction mixture was concentrated, the residue was washed with n-hexane to yield 3.12 g of brown crystals, which were recrystallized from isopropyl ether to give brown prisms, mp 111°–113° C.

IR spectrum $\nu$ (KBr) cm$^{-1}$: 1730 mass spectrum m/z: 378 (M+)

NMR spectrum $\delta$ (CDCl$_3$) ppm: 1.25(3H,t,J=7.5 Hz),2.00–2.90 (12H,m),4.14(2H,q,J=7.5 Hz),4.83(1H,d, J=12 Hz ), 5.65(1H ,d,J=12 Hz), 6.79(1H,dd,J=8.5,1 Hz),6.86(1H,td,J=7.5,1 Hz),7.05–7.15(2H,m),7.21 (1H,dd,J=7.5,5Hz),7.67(1H,dd,J=7.5,2 Hz),8.54(1H,dd,J=5,2 Hz)

High resolution mass spectrum for: $C_{23}H_{26}N_2O_3$ Calculated m/z: 378.1943 Found m/z: 378.1939

(2)
3-[4-(5,11-Dihydrobenz[b]oxepino[4,3-b]pyridin-11-ylidene) piperidino]propionic Acid.Hydrochloride The mixture of 2.50 g of ethyl 3-[4-(5,11-dihydrobenz[b]oxepino[4,3-b]pyridin-11-ylidene)-piperidino]propionate and 6.6 ml of 2N aqueous sodium hydroxide solution in 25 ml of methanol was stirred at room temperature for 2.5 hours. The reaction mixture was adjusted to pH 4 with 10% hydrochloric acid and then evaporated to dryness and the resulting residue was extracted with hot ethanol. The extract was concentrated to yield 2.52 g of red crystals, which were recrystallized from ethanol to give pale brown crystals, mp 203°–206° C.

Analysis for $C_{21}H_{22}N_2O_3 \cdot HCl \cdot H_2O$ Calculated C, 62.30; H, 6.22; N, 6.92 Found C, 62.51; H, 6.00; N, 7.02.

Example 2:
3-[4-(8-Fluoro-5,11-dihydrobenz[b]oxepino[4,3-b]pyridin-11-ylidene)piperidino]propionic Acid (1) Ethyl 3-[4-(8-Fluoro-5,11-dihydrobenz[b]oxepino[4,3-b]pyridin-11-ylidene)piperidino]propionate Title compound was prepared in the same manner as described in Example 1-(1).

Yellowish brown oil

IR spectrum $\nu$ (liq) cm$^{-1}$: 1732

NMR spectrum $\delta$ (CDCl$_3$) ppm: 1.26(3H,t,J=7.5 Hz),2.11–2.73 (12H,m),4.14(2H,q,J=7.5 Hz),4.83(1H,d,J=12.5 Hz),5.63(1H,d, J=12.5 Hz),6.51(1H,dd,J=10.5,2.5 Hz),6.57–6.61(1H,m),7.03–7.06(1H,m), 7.22(1H,dd,J=7.5,5 Hz),7.68(1H,dd,J=7.5,2 Hz),8.55(1H,dd,J=5,2 Hz)

High resolution mass spectrum for: $C_{23}H_{25}FN_2O_3$ Calculated m/z: 396.1849 Found m/z: 396.1852.

(2)
3-[4-(8-Fluoro-5,11-dihydrobenz[b]oxepino[4,3-b]pyridin-11-ylidene)piperidino]propionic Acid Title compound was prepared in the same manner as described in Example 1-(2).

Slightly purple crystals, mp 160°–161° C. (MeOH)

Analysis for $C_{21}H_{21}FN_2O_3$ Calculated C, 68.47; H, 5.75; N, 7.60 Found C, 68.31; H, 5.75; N, 7.50.

Example 3:
3-[4-(9-Fluoro-5,11-dihydrobenz[b]oxepino[4,3-b]pyridin-11-ylidene)piperidino]propionic Acid (1) Ethyl 3-[4-(9-Fluoro-5,11-dihydrobenz[b]oxepino[4,3-b]pyridin-11-ylidene)piperidino]propionate Title compound was prepared in the same manner as described in Example 1-(1).

Pale orange crystals, mp 100°–105° C. ( iso-Pr$_2$O)

Analysis for $C_{23}H_{25}FN_2O_3$ Calculated C, 69.68; H, 6.36; N, 7.07 Found C, 69.67; H, 6.51; N, 6.88.

(2)
3-[4-(9-Fluoro-5,11-dihydrobenz[b]oxepino[4,3-b]pyridin-11-ylidene)piperidino]propionic Acid Title compound was prepared in the same manner as described in Example 1-(2).

Pale brown needles, mp 121°–124° C. (EtOH)

Analysis for $C_{21}H_{21}FN_2O_3 \cdot 9/4 H_2O$ Calculated C, 61.68; H, 6.29; N, 6.85 Found C, 61.67; H, 6.03; N, 6.87

Example 4:
3-[4-(7-Chloro-5,11-dihydrobenz[b]oxepino[4,3-b]pyridin-11-ylidene)piperidino]propionic Acid . Hydrochloride (1) Ethyl 3-[4-(7-Chloro-5,11-dihydrobenz[b]oxepino[4,3-b]pyridin-11-ylidene )piperidino]propionate Title compound was prepared in the same manner as described in Example 1-( 1 ).

Colorless prisms, mp 110.5°–111.5° C. ( Acetone-Et$_2$O)

Analysis for $C_{23}H_{25}ClN_2O_3$ Calculated C, 66.90; H, 6.10; N, 6.78 Found C, 66.85; H, 6.17; N, 6.80.

(2)
3-[4-(7-Chloro-5,11-dihydrobenz[b]oxepino[4,3-b]pyridin-11-ylidene)piperidino]propionic Acid. Hydrochloride Title compound was prepared in the same manner as described in Example 1-( 2 ).

Colorless needles, mp 249.5°–252.5° C. (decomposition, EtOH-H$_2$O)

Analysis for C$_{21}$H$_{21}$ClN$_2$O$_3$.HCl Calculated C, 59.87; H, 5.26; N, 6.65 Found C, 59.78; H, 5.19; N, 6.65.

Example 5:
3-[4-(8-Chloro-5,11-dihydrobenz[b]oxepino[4,3-b]pyridin-11-ylidene)piperidino]propionic Acid . Hydrochloride (1) Ethyl 3-[4-(8-Chloro-5,11-dihydrobenz[b]oxepino[4,3-b]pyridin-11-ylidene)piperidino]propionate. Hydrochloride Title compound was prepared in the same manner as described in Example 1-(1).

Colorless crystals, mp 210°–213° C. (decomposition, iso-PrOH)

Analysis for C$_{23}$H$_{25}$ClN$_2$O$_3$.HCl Calculated C, 61.47; H, 5.83; N, 6.23 Found C, 61.34; H, 5.80; N, 6.18.

(2)
3-[4-(8-Chloro-5,11-dihydrobenz[b]oxepino[4,3-b]pyridin-11-ylidene)piperidino]propionic Acid. Hydrochloride Title compound was prepared in the same manner as described in Example 1-(2).

Colorless crystals, mp 257°–260° C. (decomposition, MeOH)

Analysis for C$_{21}$H$_{21}$ClN$_2$O$_3$.HCl Calculated C, 59.87; H, 5.26; N, 6.65 Found C, 59.75; H, 5.28; N, 6.58.

Example 6:
3-[4-(9-Chloro-5,11-dihydrobenz[b]oxepino[4,3-b]pyridin-11-ylidene)piperidino]propionic Acid (1) Ethyl 3-[4-(9-Chloro-5,11-dihydrobenz[b]oxepino[4,3-b]pyridin-11-ylidene)piperidino]propionate Title compound was prepared in the same manner as described in Example 1-(1).

Pale orange crystals, mp 118°–119° C. (AcOEt-iso-Pr$_2$O)

Analysis for C$_{23}$H$_{25}$ClN$_2$O$_3$ Calculated C, 66.90; H, 6.10; N, 6.78 Found C, 66.83; H, 6.12; N, 6.74.

(2)
3-[4-(9-Chloro-5,11-dihydrobenz[b]oxepino[4,3-b]pyridin-11-ylidene)piperidino]propionic Acid Title compound was prepared in the same manner as described in Example 1-(2).

Colorless needles, mp 198°–199.5° C. (MeOH)

Analysis for C$_{21}$H$_{21}$ClN$_2$O$_3$.3/2H$_2$O Calculated C, 61.24; H, 5.87; N, 6.80 Found C, 61.28; H, 5.79; N, 6.88.

Example 7:
3-[4-(8-Bromo-5,11-dihydrobenz[b]oxepino[4,3-b]pyridin-11-ylidene)piperidino]propionic Acid (1) Ethyl 3-[4-(8-Bromo-5,11-dihydrobenz[b]oxepino[4,3-b]pyridin-11-ylidene)piperidino]propionate Title compound was prepared in the same manner as described in Example 1-(1).

Slightly purple amorphous

IR spectrum ν (liq) cm$^{-1}$: 1734

NMR spectrum δ (CDCl$_3$) ppm: 1.25(3H,t,J=7 Hz),2.07–2.82 (12H,m),4.14 (2H,q,J=7 Hz),4.83(1H,d,J=12.5 Hz),5.62(1H,d,J=12.5 Hz), 6.95–6.99(3H,m),7.23(1H,dd ,J=7.5,5 Hz),7.68(1H,dd,J=7.5,2 Hz ),8.55 (1H,dd,J=5,2 Hz)

High resolution mass spectrum for: C$_{23}$H$_{25}$BrN$_2$O$_3$ Calculated m/z: 456.1049 , 458.1029 Found m/z: 456.1034 , 458.1038.

(2)
3-[4-(8-Bromo-5,11-dihydrobenz[b]oxepino[4,3-b]pyridin-11-ylidene)piperidino]propionic Acid Title compound was prepared in the same manner as described in Example 1-(2).

Colorless crystals, mp 137°–139° C. (iso-PrOH)

Analysis for C$_{21}$H$_{21}$BrN$_2$O$_3$.4/3H$_2$O Calculated C, 55.64; H, 5.26; N, 6.18 Found C, 55.45; H, 4.97; N, 6.42.

Example 8:
3-[4-(10H-benzo[b]pyrano[3,2-b]pyridin-10-ylidene) piperidino]propionic Acid (1) Ethyl 3-[4-(10H-Benzo[b]pyrano[3,2-b]pyridin-10-ylidene) piperidino]propionate . Hydrochloride Title compound was prepared in the same manner as described in Example 1-(1).

Brown needles, mp 179°–181° C. (acetone-AcOEt)

Analysis for C$_{22}$H$_{24}$N$_2$O$_3$.HCl Calculated C, 65.91; H, 6.29; N, 6.99 Found C, 65.79; H, 6.06; N, 6.84.

(2) 3-[4-(10H-Benzo[b]pyrano[3,2-b]pyridin-10-ylidene) piperidino]propionic Acid Title compound was prepared in the same manner as described in Example 1-(2).

Pale brown prisms, mp 178°–181° C. (MeOH)

Analysis for C$_{20}$H$_{20}$N$_2$O$_3$.7/4H$_2$O Calculated C, 65.29; H, 6.44; N, 7.61 Found C, 65.02; H, 6.39; N, 7.57.

Example 9:
3-[4-(7-Fluoro-10H-benzo[b]pyrano[3,2-b]pyridin-10-ylidene)piperidino]propionic Acid (1) Ethyl 3-[4-(7-Fluoro-10H-benzo[b]pyrano[3,2-b]pyridin-10-ylidene)piperidino]propionate. Sesquifumarate Title compound was prepared in the same manner as described in Example 1-(1).

Pale yellow crystals, mp 159.5°–161.5° C. (AcOEt)

Analysis for C$_{22}$H$_{23}$FN$_2$O$_3$.3/2C$_4$H$_4$O$_4$ Calculated C, 60.43; H, 5.25; N, 5.03 Found C, 60.39; H, 5.28; N, 5.06.

(2)
3-[4-(7-Fluoro-10H-benzo[b]pyrano[3,2-b]pyridin-10-ylidene) piperidino]propionic Acid Title compound was prepared in the same manner as described in Example 1-(2).

Yellow prisms, mp 111°–114° C. (EtOH)

Analysis for C$_{20}$H$_{19}$FN$_2$O$_3$.9/4H$_2$O Calculated C, 60.83; H, 6.00; N, 7.09 Found C, 61.07; H, 5.89; N, 7.18.

Example 10:
4-[4-(8-Fluoro-5,11-dihydrobenz[b]oxepino[4,3-b]pyridin-11-ylidene)piperidino]butyric Acid (1) Ethyl 4-[4-(8-Fluoro-5,11-dihydrobenz[b]oxepino[4,3-b]pyridin-11-ylidene)piperidino]butyrate A mixture of 2.00 g of 8-fluoro-5,11-dihydro-11-(4-piperidylidene)benz[b]oxepino[4,3-b]pyridine, 1.16 ml of ethyl 4-bromobutyate, and 1.12 g of potassium carbonate in 14 ml of N,N-dimethylformamide was stirred at 50° C. for 4.5 hours. The reaction mixture was diluted with water and then extracted with ether. The organic later was washed with brine, dried over anhydrous sodium sulfate, and then concentrated. The residue was purified by column chromatography on silica gel [eluent: methylene chloride-methanol (70:1→50:1→20:1)] to yield 2.61 g of brown crystals, which were recrystallized from isopropyl ether to give pale brown prisms, mp 72°–74.5° C.

Analysis for $C_{24}H_{27}FN_2O_3$ Calculated C, 70.22; H, 6.63; N, 6.82 Found C, 70.27; H, 6.66; N, 6.79.

(2)

4-[4-(8-Fluoro-5,11-dihydrobenz[b]oxepino[4,3-b]pyridin-11-ylidene)piperidino]butyric Acid Title compound was prepared in the same manner as described in Example 1-(2).

Pale pink crystals, mp 126.5°–129.5° C. (acetone-iso-Pr₂O)

Analysis for $C_{22}H_{23}FN_2O_3 \cdot \frac{3}{4}H_2O$ Calculated C, 66.74; H, 6.24; N, 7.08 Found C, 66.89; H, 6.16; N, 7.02.

Example 11:
5-[4-(8-Fluoro-5,11-dihydrobenz[b]oxepino[4,3-b]pyridin-11-ylidene)piperidino]valetic Acid (1) Ethyl 5-[4-(8-Fluoro-5,11-dihydrobenz[b]oxepino[4,3-b]pyridin-11-ylidene)piperidino]valerate Title compound was prepared in the same manner as described in Example 10-(1).

Brown oil

IR spectrum $\nu$ (liq) cm⁻¹: 1732

NMR spectrum $\delta$ (CDCl₃) ppm: 1.25(3H,t,J=7.5 Hz),1.50–1.72 (4H,m),2.27–2.95(12H,m),4.12(2H,q,J=7.5 Hz),4.83(1H,d ,J=12 Hz),5.62 (1H,d,J=12 Hz),6.51(1H,dd,J=10.5,2.5 Hz),6.59(1H,td,J=8.5,2.5 Hz), 7.04(1H,dd,J=8.5.6.5 Hz),7.23(1H,dd,J=8,5 Hz),7.68(1H,dd,J=8,2 Hz), 8.55(1H,dd,J=5,2 Hz)

High resolution mass spectrum for: $C_{25}H_{29}FN_2O_3$ Calculated m/z: 424.2161 Found m/z: 424.2160.

(2)

5-[4-(8-Fluoro-5,11-dihydrobenz[b]oxepino[4,3-b]pyridin-11-ylidene)piperidino]valetic Acid Title compound was prepared in the same manner as described in Example 1-(2).

Pale pink crystals, mp 104°–106.5° C. (Acetone-iso-Pr₂O)

Analysis for $C_{23}H_{25}FN_2O_3 \cdot H_2O$ Calculated C, 66.65; H, 6.57; N, 6.76 Found C, 66.77; H, 6.53; N, 6.70.

Example 12:
6-[4-(8-Fluoro-5,11-dihydrobenz[b]oxepino[4,3-b]pyridin-11-ylidene)piperidino]hexanoic Acid . Hydrochloride (1) Ethyl 6-[4-(8-Fluoro-5,11-dihydrobenz[b]oxepino[4,3-b]pyridin-11-ylidene)piperidino]hexanoate Title compound was prepared in the same manner as described in Example 10-(1).

Pale brown needles, mp 60.5°–62.5° C. (n-Hexane)

Analysis for $C_{26}H_{31}FN_2O_3$ Calculated C, 71.21; H, 7.13; N, 6.39 Found C, 71.26; H, 7.19; N, 6.35.

(2)

6-[4-(8-Fluoro-5,11-dihydrobenz[b]oxepino[4,3-b]pyridin-11-ylidene)piperidino]hexanoic Acid . Hydrochloride Title compound was prepared in the same manner as described in Example 1-(2).

Colorless needles, mp 240°–243° C. (MeOH)

Analysis for $C_{24}H_{27}FN_2O_3 \cdot HCl$ Calculated C, 64.50; H, 6.31; N, 6.27 Found C, 64.45; H, 6.30; N, 6.26.

Example 13:
3-[4-(8-Fluoro-5,11-dihydrobenz[b]oxepino[4,3-b]pyridin-11-ylidene)piperidino]butyric Acid (1) Ethyl 3-[4-(8-Fluoro-5,11-dihydrobenz[b]oxepino[4,3-b]pyridin-11-ylidene)piperidino]butyrate Title compound was prepared in the same manner as described in Example 10-(1).

Yellowish brown oil

IR spectrum $\nu$ (liq) cm⁻¹: 1734

NMR spectrum $\delta$ (CDCl₃) ppm: 1.03(3H,d,J=6.5 Hz)1.23–1.30 (3H,m),2.16–2.84(10H,m),3.-15–3.25(1H,m),4.08–4.18(2H,m),4.82(1H, d,J=12 Hz),5.64(1H,d,J=12 Hz),6.50(1H,dd,J=10.5,2.5 Hz),6.58(1H,td, J=8.5,2.5 Hz),7.05(1H,dd,J=8.5,7.5 Hz),7.21(1H,dd,J=7.5,5 Hz),7.67 (1H,dd,J=7.5,2 Hz),8.55(1H,d,J=4 Hz)

High resolution mass spectrum for: $C_{24}H_{27}FN_2O_3$ Calculated m/z: 410.2006 Found m/z: 410.2006.

(2)

3-[4-(8-Fluoro-5,11-dihydrobenz[b]oxepino[4,3-b]pyridin-11-ylidene)piperidino]butyric Acid Title compound was prepared in the same manner as described in Example 1-(2).

Pale pink amorphous

IR spectrum $\nu$ (KBr) cm⁻¹: 1614, 1582

NMR spectrum $\delta$ (CDCl₃) ppm: 1.09(3H,d,J=6.5 Hz),2.34–3.23 (11H,m),4.85(1H,d,J=12 Hz ),5.58(1H,d ,J=12 Hz ), 6.54( 1H,dd ,J=10.5, 2.5 Hz),6.16(1H,td,J=8.5,2.5 Hz),7.03(1H,ddd,J=8.5,6.5,1.5 Hz),7.26 (1H,dd,J=7.5,5 Hz),7.69(1H,dd,J=7.5,1.5 Hz),8.56(1H,dd,J=5,1.5 Hz)

High resolution mass spectrum for: $C_{22}H_{23}FN_2O_3$ Calculated m/z: 382.1693 Found m/z: 382.1696

Example 14:
3-[4-(8-Fluoro-5,11-dihydrobenz[b]oxepino[4,3-b]pyridin-11-ylidene)piperidino]-2-methylpropionic Acid (1) Ethyl 3-[4-(8-Fluoro-5,11-dihydrobenz[b]oxepino[4,3-b]pyridin-11-ylidene)piperidino]-2-methylpropionate Title compound was prepared in the same manner as described in Example 10-(1).

Dark brown oil,

IR spectrum $\nu$ (liq) cm⁻¹: 1732

NMR spectrum $\delta$ (CDCl₃) ppm: 0.82–1.08(1H,m),1.14(3H,d, J=6.5 Hz),1.26(3H,t,J=7.5 Hz),1.80–2.87(8H,m),3.97–4.08(2H,m),4.-08–4.20(2H,m),4.82(1H,d,J=12 Hz),5.63(1H,d,J=12 Hz),6.50(1H,dd,J=10.5, 3 Hz),6.58(1H,td,J=8,3 Hz),7.04(1H,ddd,J=8.5,6.5,2 Hz),7.22(1H,dd, J=7.5,5 Hz),7.67(1H,dd,J=7.5,2 Hz),8.55(1H,d,J=5 Hz)

High resolution mass spectrum for: $C_{24}H_{27}FN_2O_3$ Calculated m/z: 410. 2006 Found m/z: 410.2010.

(2)

3-[4-(8-Fluoro-5,11-dihydrobenz[b]oxepino[4,3-b]pyridin-11-ylidene)piperidino]-2-methylpropionic Acid Title compound was prepared in the same manner as described in Example 1-(2).

Pale pink prisms, mp 192.5°–194.5° C. (iso-PrOH)

Analysis for $C_{22}H_{23}FN_2O_3 \cdot \frac{1}{4}H_2O$ Calculated C, 68.29; H, 6.12; N, 7.24 Found C, 68.36; H, 6.11; N, 7.15.

Example 15:
4-[4-(8-Fluoro-5,11-dihydrobenz[b]oxepino[4,3-b]pyridin-11-ylidene)piperidino]-3-methylbutyric Acid (1) Ethyl 4-[4-(8-Fluoro-5,11-dihydrobenz[b]oxepino[4,3-b]pyridin-11-ylidene)piperidino]-3-methylbutyrate Title compound was prepared in the same manner as described in Example 10-(1).
Brown oil
IR spectrum $\nu$ (liq) cm$^{-1}$: 1732
NMR spectrum $\delta$ (CDCl$_3$) ppm: 0.93(3H,d,J=6.5 Hz),1.21–1.30 (3H,m),1.89–2.33(7H,m),2.39–2.98(6H,m),4.07–4.18(2H,m),4.82(1H,d, J=12 Hz),5.64(1H,d,J=12 Hz),6.50(1H,dd,J=10.5,2.5 Hz),6.58(1H,td, J=8.5,2.5 Hz),7.05(1H,dd,J=8.5,6.5 Hz),7.22(1H,dd,J=7.5,5 Hz),7.67 (1H,dd,J=7.5,2 Hz),8.55(1H,dd,J=5,2 Hz)
High resolution mass spectrum for: C$_{25}$H$_{29}$FN$_2$O$_3$ Calculated m/z: 424.2163 Found m/z: 424.2163.

(2)
4-[4-(8-Fluoro-5,11-dihydrobenz[b]oxepino[4,3-b]pyridin-11-ylidene)piperidino]-3-methylbutyric Acid Title compound was prepared in the same manner as described in Example 1-(2).
Pale brown amorphous
IR spectrum $\nu$ (KBr) cm$^{-1}$: 1612, 1580
NMR spectrum $\delta$ (CDCl$_3$) ppm: 0.97(3H,d,J=6.5 Hz),2.16–3.13 (13H,m),4.85(1H,d,J=13 Hz),5.56(1H,d,J=13 Hz),6.53(1H,dd,J=10.5, 2.5 Hz),6.61(1H,td,J=8.5,6.5 Hz),7.01(1H,dd,J=8.5,6.5, Hz),7.26(1H, dd,J=7.5,5 Hz),7.69(1H,dd,J=7.5,2 Hz),8.55(1H,d,J=5 Hz)
High resolution mass spectrum for: C$_{23}$H$_{25}$FN$_2$O$_3$ Calculated m/z: 396.1849 Found m/z: 396.1855.

Example 16:
4-[4-(9-Fluoro-5,11-dihydrobenz[b]oxepino[4,3-b]pyridin-11-ylidene)piperidino]butyric Acid. Hydrochloride (1) Ethyl 4-[4-(9-Fluoro-5,11-dihydrobenz[b]oxepino[4,3-b]pyridin-11-ylidene)piperidino]butyrate Title compound was prepared in the same manner as described in Example 10-(1).
Pale brown needles, mp 87°–90° C. (iso-Pr$_2$O)
Analysis for C$_{24}$H$_{27}$FN$_2$O$_3$ Calculated C, 70.22; H, 6.63; N, 6.82 Found C, 70.15; H, 6.61; N, 6.77.

(2)
4-[4-(9-Fluoro-5,11-dihydrobenz[b]oxepino[4,3-b]pyridin-11-ylidene)piperidino]butyric Acid. Hydrochloride Title compound was prepared in the same manner as described in Example 1-(2).
Pale yellow crystals, mp 235°–238° C. (MeOH-Et$_2$O)
Analysis for C$_{22}$H$_{23}$FN$_2$O$_3$.HCl.$\frac{3}{4}$H$_2$O Calculated C, 61.11; H, 5.94; N, 6.48 Found C, 61.05; H, 5.71; N, 6.48.

Example 17:
4-[4-(7-Chloro-5,11-dihydrobenz[b]oxepino[4,3-b]pyridin-11-ylidene)piperidino]butyric Acid. Hydrochloride
(1) Ethyl 4-[4-(7-Chloro-5,11-dihydrobenz[b]oxepino[4,3-b]pyridin-11-ylidene)piperidino]butyrate Title compound was prepared in the same manner as described in Example 10-(1).
Colorless needles, mp 77°–78.5° C. (Acetone-Et$_2$O)
Analysis for C$_{24}$H$_{27}$ClN$_2$O$_3$ Calculated C, 67.52; H, 6.37; N, 6.56 Found C, 67.53; H, 6.48; N, 6.50.

(2)
4-[4-(7-Chloro-5,11-dihydrobenz[b]oxepino[4,3-b]pyridin-11-ylidene)piperidino]butyric Acid. Hydrochloride Title compound was prepared in the same manner as described in Example 1-(2).
Colorless needles, mp 249.5°–252.5° C. (decomposition, acetone-H$_2$O)
Analysis for C$_{22}$H$_{23}$ClN$_2$O$_3$.HCl.2H$_2$O Calculated C, 56.06; H, 5.99; N, 5.94 Found C, 55.94; H, 5.81; N, 5.93.

Example 18:
4-[4-(8-Chloro-5,11-dihydrobenz[b]oxepino[4,3-b]pyridin-11-ylidene)piperidino]butyric Acid. Hydrochloride (1) Ethyl 4-[4-(8-Chloro-5,11-dihydrobenz[b]oxepino[4,3-b]pyridin-11-ylidene)piperidino]butyrate Title compound was prepared in the same manner as described in Example 10-(1).
Pale orange crystals, mp 102°–103° C. (Acetone-iso-Pr$_2$O)
Analysis for C$_{24}$H$_{27}$ClN$_2$O$_3$ Calculated C, 67.52; H, 6.37; N, 6.56 Found C, 67.34; H, 6.32; N, 6.62

(2)
4-[4-(8-Chloro-5,11-dihydrobenz[b]oxepino[4,3-b]pyridin-11-ylidene)piperidino]butyric Acid. Hydrochloride Title compound was prepared in the same manner as described in Example 1-(2).
Colorless prisms, mp 228°–229.5° C. (Acetone-H$_2$O)
Analysis for C$_{22}$H$_{23}$ClN$_2$O$_3$.HCl.$\frac{3}{4}$H$_2$O Calculated C, 58.86; H, 5.73; N, 6.23 Found C, 58.95; H, 5.50; N, 6.26.

Example 19:
4-[4-(9-Chloro-5,11-dihydrobenz[b]oxepino[4,3-b]pyridin-11-ylidene)piperidino]butyric Acid. Hydrochloride (1) Ethyl 4-[4-(9-Chloro-5,11-dihydrobenz[b]oxepino[4,3-b]pyridin-11-ylidene)piperidino]butyrate Title compound was prepared in the same manner as described in Example 10-(1).
Colorless needles, mp 106°–107° C. (AcOEt-iso-Pr$_2$O)
Analysis for C$_{24}$H$_{27}$ClN$_2$O$_3$ Calculated C, 67.52; H, 6.37; N, 6.56 Found C, 67.53; H, 6.33; N, 6.54.

(2) 4-[4-(9-Chloro-5,11-dihydrobenz[b]oxepino[4,3-b]pyridin-11-ylidene)piperidino]butytic Acid. Hydrochloride Title compound was prepared in the same manner described in Example 1-(2).
Colorless prisms, mp 242°–245.5° C. (EtOH-H$_2$O)
Analysis for C$_{22}$H$_{23}$ClN$_2$O$_3$.HCl.H$_2$O Calculated C, 58.28; H, 5.78; N, 6.18 Found C, 58.50; H, 5.68; N, 6.15.

Example 20:
5-[4-(8-Chloro-5,11-dihydrobenz[b]oxepino[4,3-b]pyridin-11-ylidene)piperidino]valeric Acid. Hydrochloride (1) Ethyl 5-[4-(8-Chloro-5,11-dihydrobenz[b]oxepino[4,3-b]pyridin-11-ylidene)piperidino]valerate. Hydrochloride Title compound was prepared in the same manner as described in Example 10-(1).
Pale yellow crystals, mp 224.5°–227° C. (decomposition, EtOH-Et$_2$O)
Analysis for C$_{25}$H$_{29}$ClN$_2$O$_3$.HCl.$\frac{1}{2}$H$_2$O Calculated C, 61.73; H, 6.42; N, 5.76 Found C, 61.64; H, 6.56; N, 5.90.

(2) 5-[4-(8-Chloro-5,11-dihydrobenz[b]oxepino[4,3-b]pyridin-11-ylidene)piperidino]valetic Acid. Hydrochloride Title compound was prepared in the same manner as described in Example 1-(2).

Colorless needles, mp 215.5°–217° C. (EtOH-$H_2O$)

Analysis for $C_{23}H_{25}ClN_2O_3.HCl.5/4H_2O$ Calculated C, 58.54; H, 6.09; N, 5.94 Found C, 58.72; H, 5.86; N, 6.02.

Example 21:
6-[4-(8-Chloro-5,11-dihydrobenz[b]oxepino[4,3-b]pyridin-11-ylidene)piperidino]hexanoic Acid . Hydrochloride (1) Ethyl 6-[4-(8-Chloro-5,11-dihydrobenz[b]oxepino[4,3-b]pyridin-11-ylidene)piperidino]hexanoate Title compound was prepared in the same manner as described in Example 10-(1).

Pale brown crystals, mp 104°–106° C. ($Et_2O$)

Analysis for $C_{26}H_{31}ClN_2O_3$ Calculated C, 68.63; H, 6.87; N, 6.16 Found C, 68.50; H, 6.86; N, 6.16.

(2) 6-[4-(8-Chloro-5,11-dihydrobenz[b]oxepino[4,3-b]pyridin-11-ylidene)piperidino]hexanoic Acid . Hydrochloride Title compound was prepared in the same manner as described in Example 1-(2).

Colorless crystals, mp 238.5°–240° C. (EtOH-$H_2O$)

Analysis for $C_{24}H_{27}ClN_2O_3.HCl.\frac{1}{4}H_2O$ Calculated C, 61.61; H, 6.14; N, 5.99 Found C, 61.75; H, 6.00; N, 6.01.

Example 22:
4-[4-(10H-Benzo[b]pyrano[3,2-b]pyridin-10-ylidene)piperidino]butyric Acid . Hydrochloride (1) Ethyl 4-[4-(10H-Benzo[b]pyrano[3,2-b]pyridin-10-ylidene) piperidino]butyrate Title compound was prepared in the same manner as described in Example 1-(1).

Brown oil

IR spectrum $\nu$ (liq) $cm^{-1}$: 1734

NMR spectrum $\delta$ ($CDCl_3$) ppm: 1.25(3H,t,J=7.5 Hz),1.75–1.90(2H,m),2.35(2H,t,J=7.5 Hz),2.30–2.58(6H,m),2.80–2.90(2H,m),3.15–3.30(2H,m),4.13(2H,q,J=7.5 Hz),7.11–7.28(4H,m), 7.36 (1H,dd,J=7.5,1.5 Hz),7.44(1H,dd,J=7.5,1.5 Hz),8.37(1H,dd,J=4.5,1.5 Hz )

(2) 4-[4-(10H-Benzo[b]pyrano[3,2-b]pyridin-10-ylidene) piperidino]butyric Acid . Hydrochloride Title compound was prepared in the same manner as described in Example 1-(2).

Pale brown crystals, mp 214°–216° C. (MeOH)

Analysis for $C_{21}H_{22}N_2O_3.HCl$ Calculated C, 65.20; H, 5.99; N, 7.24 Found C, 64.93; H, 6.00; N, 7.17.

Example 23:
4-[4-(7-Fluoro-10H-benzo[b]pyrano[3,2-b]pyridin-10-ylidene)piperidino]butyric Acid (1) Ethyl 4-[4-(7-Fluoro-10H-benzo[b]pyrano[3,2-b]pyridin-10-ylidene)piperidino]butyrate Title compound was prepared in the same manner as described in Example 10-(1).

Dark orange oil

IR spectrum $\nu$ (liq) $cm^{-1}$: 1734

NMR spectrum $\delta$ ($CDCl_3$) ppm: 1.26(3H,d,J=7 Hz),1.75–1.86 (2H,m),2.26–2.51(8H,m),2.76–2.78(2H,m),3.17–3.20(2H,m),4.13(2H,q, J=7 Hz),6.86(1H,td,J=8.5,2.5 Hz),6.91(1H,dd,J=8.5,2.5 Hz),7.17(1H,dd, J=8,5 Hz),7.30(1H,dd,J=8.5,6 Hz),7.43(1H,dd,J=8,1.5 Hz),8.39(1H,dd, J=5,1.5 Hz)

High resolution mass spectrum for: $C_{23}H_{25}FN_2O_3$ Calculated m/z: 396.1849 Found m/z: 396.1843.

(2) 4-[4-(7-Fluoro-10H-benzo[b]pyrano[3,2-b]pyridin-10-ylidene) piperidino]butyric Acid Title compound was prepared in the same manner as described in Example 1-(2).

Pale pink needles, mp 207°–210° C. (MeOH-$Et_2O$)

Analysis for $C_{21}H_{21}FN_2O_3.HCl$ Calculated C, 62.30; H, 5.48; N, 6.92 Found C, 62.17; H, 5.55; N, 6.93.

Example 24:
3-[4-(8-Fluoro-5,11-dihydrobenz[b]oxepino[4,3-b]pyridin-11-ylidene)piperidino]propionic Acid. Dihydrobromide (1) 1,1-Dimethylethyl 3-[4-(8-Fluoro-5,11-dihydrobenz[b]oxepino[4,3-b]pyridin-11-ylidene)piperidino]propionate A mixture of 4.40 g of 8-fluoro-5,11-dihydro-11-(4-piperidylidene)benz[b]oxepino[4,3-b]pyridine and 3.26 ml of 1,1-dimethylethyl acrylate in 26.4 ml of isopropanol was refluxed for 2 hours. The reaction mixture was concentrated to yield 6.46 g of pale brown amorphous.

(2) 3-[4-(8-Fluoro-5,11-dihydrobenz[b]oxepino[4,3-b]pyridin-11-ylidene)piperidino]propionic Acid. Dihydrobromide To a solution of 6.25 g of above-obtained 1,1-dimethylethyl 3-[4-(8-fluoro-5,11-dihydrobenz[b]oxepino[4,3-b]pyridin-11-ylidene)piperidino]propionate in 25 ml of 1,2-dichloroethane, 25 ml of 25% hydrogen bromide/acetic acid solution was added dropwise at room temperature, and the mixture was stirred at room temperature for 30 min. The resultant crystals were collected by filtration and washed with acetone to yield 7.32 g of slightly brown crystals, mp 204.5°–207.5° C.

Analysis for $C_{21}H_{21}FN_2O_3.2HBr.H_2O$ Calculated C, 46.01; H, 4.60; N, 5.11 Found C, 46.29; H, 4.36; N, 5.21.

Example 25

The pharmaceutical composition of the present invention in the form of a tablet is prepared in an ordinary manner using the following ingredients:

| Compound of the present invention | 20 mg |
| --- | --- |
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |
| | 120 mg |

Example 26

The pharmaceutical composition of the present invention in the form of a capsule is prepared in an ordinary manner using the following ingredients:

| Compound of the present invention | 10 mg |
| --- | --- |
| Lactose | q.s. |
| Calcium carboxymethylcellulose | 15 mg |

-continued

| | |
|---|---|
| Hydroxypropylcellulose | 2 mg |
| Magnesium stearate | 2 mg |
| | 100 mg |

Example 27

The pharmaceutical composition of the present invention in the form of powder is prepared in an ordinary manner using the following ingredients:

| | |
|---|---|
| Compound of the present invention | 40 mg |
| Lactose | q.s. |
| D-Mannitol | 500 mg |
| Hydroxypropylcellulose | 5 mg |
| Talc | 2 mg |
| | 1000 mg |

Example 28

The pharmaceutical composition of the present invention in the form of injection is prepared in an ordinary manner using the following ingredients:

| | |
|---|---|
| Compound of the present invention | 5 mg |
| Glucose | 50 mg |
| Hydrochloric acid | q.s. |
| Distilled water for injection | q.s. |
| | 2 ml |

Example 29

The pharmaceutical composition of the present invention in the form of suppository is prepared in an ordinary manner using the following ingredients:

| | |
|---|---|
| Compound of the present invention | 10 mg |
| Hard fat | 1290 mg |
| | 1300 mg |

Example 30

The pharmaceutical composition of the present invention in the form of plaster is prepared in an ordinary manner using the following ingredients:

| | |
|---|---|
| Compound of the present invention | 40 mg |
| Gelatin | 1100 mg |
| Polyvinylalcohol | 250 mg |
| Methylcellulose | 100 mg |
| Glycerin | 1500 mg |
| Kaolin | 850 mg |
| Sodium polyacrylate | 50 mg |
| Polybutene | 150 mg |
| Purified water | 960 mg |
| | 5000 mg |

What is claimed is:

1. An amphoteric tricyclic compound represented by the following formula:

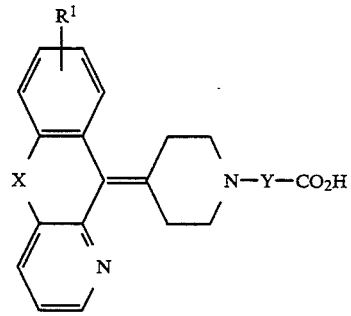

wherein $R^1$ represents a hydrogen atom or a halogen atom; X represents —O—, —CH$_2$O—, or —OCH$_2$—; and Y represents a $C_2$-$C_5$ alkylene group which may optionally be substituted with a lower alkyl group, and a pharmacologically acceptable salt thereof.

2. 3-[4-(8-Fluoro-5,11-dihydrobenz[b]oxepino[4,3-b]pyridin-11-ylidene)piperidino]propionic acid and a pharmacologically acceptable salt thereof.

3. 3-[4-(8-Chloro-5,11-dihydrobenz[b]oxepino[4,3-b]pyridin-11-ylidene)piperidino]propionic acid and a pharmacologically acceptable salt thereof.

4. A pharmaceutical composition comprising an effective amount of an amphoteric tricyclic compound represented by the following formula:

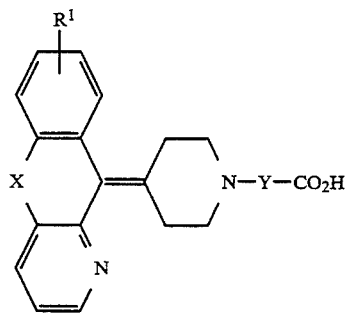

wherein $R^1$ represents a hydrogen atom or a halogen atom; X represents —O—, —CH$_2$O—, or —OCH$_2$—; and Y represents a $C_2$-$C_5$ alkylene group which may optionally be substituted with a lower alkyl group, or a pharmacologically acceptable salt thereof together with a pharmaceutically acceptable carrier or coating.

5. A method for the treatment of an allergic disease comprising the step of administering to a mammal an effective amount of an amphoteric tricyclic compound represented by the following formula:

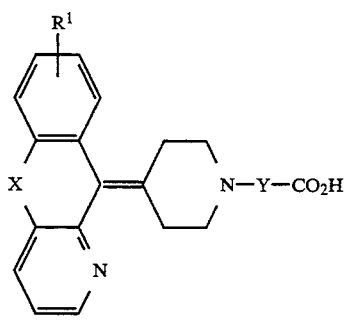

wherein $R^1$ represents a hydrogen atom or a halogen atom; X represents —O—, —CH$_2$O—, or —OCH$_2$—; and Y represents a C$_2$-C$_5$ alkylene group which may optionally be substituted with a lower alkyl group, or a pharmacologically acceptable salt thereof.

6. A method for the treatment of bronchial asthma comprising the step of administering to a mammal an effective amount of an amphoteric tricyclic compound represented by the following formula:

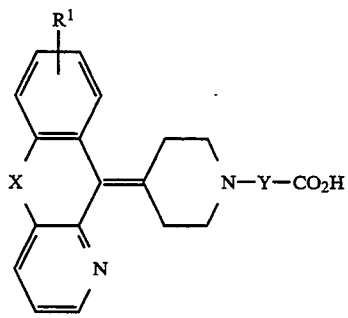

wherein $R^1$ represents a hydrogen atom or a halogen atom; X represents —O—, —CH$_2$O—, or —OCH$_2$—; and Y represents a C$_2$-C$_5$ alkylene group which may optionally be substituted with a lower alkyl group, or a pharmacologically acceptable salt thereof.

7. A method for the treatment of a histamine mediated disease comprising the step of administering to a mammal in need of such treatment, an effective amount of the pharmaceutical composition according to claim 4.

8. A method for the treatment of an allergic disease comprising the step of administering to a mammal in need of such treatment, an effective amount of the pharmaceutical composition of claim 4.

9. A method for the treatment of bronchial asthma comprising the step of administering to a mammal in need of such treatment, an effective amount of the pharmaceutical composition of claim 4.

* * * * *

UNITED STATES PATENT AND TRADEMARK OFFICE
CERTIFICATE OF CORRECTION

Page 1 of 2

PATENT NO. : 5,334,594

DATED : August 2, 1994

INVENTOR(S) : Yasuo Ito et al.

It is certified that error appears in the above-indentified patent and that said Letters Patent is hereby corrected as shown below:

Column 4, line 32, change "valetic" to --valeric--;

line 40, change "valetic" to --valeric--;

line 56, change "valetic" to --valeric--;

Column 5, line 12, change "valetic" to --valeric--;

line 44, change "valetic" to --valeric--;

Column 11, line 63, change "attopine" to --atropine--;

Column 18, line 35, change $C_{18}H_{17}ClN_2O$" to --$C_{18}H_{17}FN_2O$--;

Column 23, line 17, change "valetic" to --valeric--;

line 37, change "valetic" to --valeric--;

Column 26, line 49, change "butytic" to --butyric--;

Column 27, line 2, change "valetic" to --valeric--;

Column 28, between lines 57 and 58, insert a short, dark line separating "0.5 mg" and "120 mg";

Column 29, between lines 4 and 5, insert a short, dark line separating "2 mg" and "100 mg";

Column 29, between lines 18 and 19, insert a short, dark line separating "2 mg" and "1000 mg"; and

UNITED STATES PATENT AND TRADEMARK OFFICE
CERTIFICATE OF CORRECTION

PATENT NO. : 5,334,594
DATED : August 2, 1994
INVENTOR(S) : Yasuo Ito, et. al.

It is certified that error appears in the above-indentified patent and that said Letters Patent is hereby corrected as shown below:

Column 29, between lines 32 and 33, insert a short, dark line separating "q.s." and "2 ml".

Signed and Sealed this

Thirteenth Day of December, 1994

Attest:

*Attesting Officer*

BRUCE LEHMAN

*Commissioner of Patents and Trademarks*